United States Patent
Riscoe et al.

(10) Patent No.: US 10,584,098 B2
(45) Date of Patent: Mar. 10, 2020

(54) QUINOLONE-3-DIARYLETHERS

(71) Applicants: OREGON HEALTH & SCIENCE UNIVERSITY, Portland, OR (US); THE UNITED STATES GOVERNMENT AS REPRESENTED BY THE DEPARTMENT OF VETERANS Affairs, Washington, DC (US)

(72) Inventors: Michael Riscoe, Tualatin, OR (US); Aaron Nilsen, Portland, OR (US); Galen Miley, Portland, OR (US); Rolf Winter, Portland, OR (US); Sovitj Pou, Portland, OR (US); Jane Xu Kelly, Portland, OR (US); Rozalia Dodean, Portland, OR (US)

(73) Assignee: Oregon Health & Science University, Portland, OR (US)

( * ) Notice: Subject to any disclaimer, the term of this patent is extended or adjusted under 35 U.S.C. 154(b) by 0 days.

(21) Appl. No.: 16/110,956

(22) Filed: Aug. 23, 2018

(65) Prior Publication Data
US 2018/0362465 A1 Dec. 20, 2018
US 2019/0389802 A9 Dec. 26, 2019

Related U.S. Application Data

(63) Continuation of application No. 15/215,103, filed on Jul. 20, 2016.

(60) Provisional application No. 62/343,319, filed on May 31, 2016, provisional application No. 62/194,636, filed on Jul. 20, 2015.

(51) Int. Cl.
*C07D 215/22* (2006.01)
*C07D 405/12* (2006.01)
*C07D 409/12* (2006.01)

(52) U.S. Cl.
CPC ......... *C07D 215/22* (2013.01); *C07D 405/12* (2013.01); *C07D 409/12* (2013.01)

(58) Field of Classification Search
CPC ... C07D 215/22; C07D 405/12; C07D 409/12
See application file for complete search history.

(56) References Cited

U.S. PATENT DOCUMENTS 8,481,543 B2 7/2013 Riscoe et al.
8,598,354 B2 12/2013 Riscoe et al.
9,206,131 B2 12/2015 Riscoe et al.

FOREIGN PATENT DOCUMENTS

WO 2012069856 A1 5/2012

OTHER PUBLICATIONS

Coteron et al., Structure-Guided Lead Optimization of Triazolopyrimidine-Ring Substituents Identifies Potent Plasmodium falciparum Dihydroorotate Dehydrogenase Inhibitors with Clinical Candidate Potential, J Med Chem, 2011, 54, pp. 5540-5561.
Doggett et al., Endochin-like quinolones are highly efficacious against acute and latent experimental toxoplasmosis, PNAS, Sep. 25, 2012, vol. 109, No. 39, pp. 15936-15941.
Monastyrskyi et al., Metal-Free Arylation of Ethyl Acetoacetate with Hypervalent Diaryliodonium Salts: An Immediate Access to Diverse 3-Aryl-4(1H)-Quinolones, J Org Chem, 2015, 80, pp. 2513-2520.
Miley et al., ELQ-300 Prodrugs for Enhanced Delivery and Single-Dose Cure of Malaria, Antimicrobial Agents and Chemotherapy, Sep. 2015, vol. 59, No. 9, pp. 5555-5560.
Pou et al., Sontochin as a Guide to the Development of Drugs against Chloroquine-Resistant Malaria, Antimicrobial Agents and Chemotherapy, Jul. 2012, vol. 56, No. 7, pp. 3475-3480.
Stickles et al., Inhibition of Cytochrome bc1 as a Strategy for Single-Dose, Multi-Stage Antimalarial Therapy, Am. J. Trop. Med. Hyg., 92(6), 2015, pp. 1195-1201.
Stickles et al., Subtle Changes in Endochin-Like Quinolone Structure Alter the Site of Inhibition within the Cytochrome bc1 Complex of Plasmodium falciparum, Antimicrobial Agents and Chemotherapy, Apr. 2015, vol. 59, No. 4, pp. 1977-1982.
Nilsen et al., Quinolone-3-Diarylethers: A New Class of Antimalarial Drug, Science Translational Medicine, Mar. 20, 2013, vol. 5, Issue 177, pp. 1-13.

*Primary Examiner* — Umamaheswari Ramachandran

(57) ABSTRACT

Disclosed are derivative compounds of ELQ-300 that include an ester at position 4. These compounds have enhanced properties relative to ELQ-300. Also disclosed are pharmaceutical compositions comprising the compounds and methods of treating and preventing malaria infections involving administering the pharmaceutical compositions to the subject.

3 Claims, 1 Drawing Sheet

QUINOLONE-3-DIARYLETHERS

RELATED APPLICATIONS

U.S. Provisional Patent Application 62/194,636, filed on 20 Jul. 2015 and U.S. Provisional Patent Application 62/343,319, filed on 31 May 2016 are related to this application and are hereby incorporated by reference in their entireties. This application is a continuation of application Ser. No. 15/215,103, filed Jul. 19, 2016.

ACKNOWLEDGEMENT OF GOVERNMENT SUPPORT

Work resulting in this invention was funded by the United States government under the terms of a VA Merit Review Grant awarded to Dr. Michael Riscoe by the United States Veterans Administration and Grant Numbers R56AI100569, R01AI100569, and PR130649 awarded by the National Institutes of Health. The United States government has certain rights in this invention.

FIELD

Generally, the field is small molecule therapeutics for use in treating infectious disease. More specifically, the field is anti-parasitic compositions derived from quinolone-3-diarylethers.

BACKGROUND

Malaria remains an enormous global health problem Malaria remains one of the deadliest diseases in the world today, as it has been for thousands of years. For each of the 1 million people killed each year, hundreds of millions more suffer from severe illness (1). Spread by mosquitoes from person to person malaria remains one of the most widespread infectious diseases of our time. There are five identified species of the parasite responsible for human malaria all belonging to genus *Plasmodium*. *P. falciparum* is the dominant species in sub-Saharan Africa, and is responsible for the majority of the malaria-related deaths. *P. vivax*, known to be responsible for relapsing malaria, causes as much as 25-40% of the global malaria burden, whereas *P. ovale*, and *P. malariae* represent a small percentage of infections. A fifth species *P. knowlesi*, a species that infects subhuman primates, has Jed to human malaria, but the exact mode of transmission remains unclear.

The impact of malaria is particularly devastating in sub-Saharan Africa where its victims are primarily young children and pregnant women. This situation is worsened by the growing emergence of *Plasmodium* parasites that are resistant to multiple drugs (2). The list of drugs that are losing potency against malaria includes the quinolines—chloroquine, quinine, and mefloquine; the antifolates—pyrimethamine and sulfadoxine; and the anti-respiratory combination of atovaquone (ATV) and proguanil. In SE Asia, treatment of multidrug resistant malaria relies solely on the endoperoxide artesunate, leaving a razor thin wall of opposition to the total collapse of malaria chemotherapy. One of the greatest challenges in global health today is the development of a safe and affordable drug for treatment and prevention of malaria (3).

SUMMARY

The antimalarial drug ELQ-300 is a selective sub-nanomolar inhibitor of *Plasmodium falciparum* cytochrome bc1 complex. The effects of the drug are parasiticidal due to the requirement of cytochrome bc1 and the coenzyme Q cycle for production of pyrimidines needed for DNA and RNA synthesis. As a result, ELQ-300 exhibits an excellent parasitological profile with potent activity against all life cycle stages of *P. falciparum* including liver, bloodstream, and vector stages. Unfortunately, the challenging physical-chemical characteristics of ELQ-300 limit its potential for clinical development, i.e., a high degree of crystallinity (e.g., melting point>300° C.) and poor aqueous solubility limit oral absorption to such a degree that it has been impossible to establish a therapeutic safety window. To address the issues of high crystallinity and poor water solubility we initiated a prodrug effort focusing primarily on carbonate ester prodrugs such as the ethylcarbonate ester ELQ-337. The degree of crystallinity of the drug was significantly reduced relative to ELQ-300 (i.e., melting point for ELQ-337=150° C.) and the oral bioavailability in mice and rats was also enhanced over ELQ-300. We now wish to disclose novel alkoxycarbonyloxyalkyl ester prodrugs of ELQ-300 (and similar 4(1H)Quinolone-3-diarylether substituted derivatives such as ELQ-271, ELQ-316, and ELQ-400) with greatly reduced crystallinity as well as other features that suggest that they may be readily formulated for clinical use for treatment and prophylaxis against malaria as well as for disease eradication.

Disclosed herein are compounds of the formula:

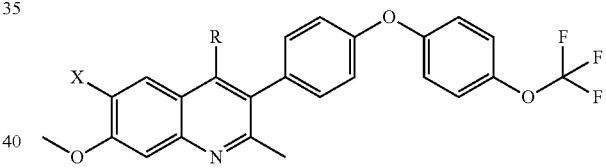

wherein X is halo and wherein R is an ester. In some examples, X is fluoro or chloro. In other examples, R is a carbonate ester. In still more examples, X is chloro and R is a carbonate ester selected from methyl carbonate; ethyl carbonate; 2-methoxyethylcarbonate; 2-(2-methoxyethoxy)ethyl carbonate; 2-(2-(2-methoxyethoxy)ethoxy)ethyl) carbonate; allyl carbonate; tert-butyl carbonate; ((2,2-dimethyl-1,3-dioxolan-4-yl)methyl) carbonate; ((2-oxo-1,3-dioxolan-4-yl)methyl carbonate; 2,3-dihydroxypropyl carbonate; or 1,1-dioxidotetrahydrothiophen-3-yl carbonate. In still further examples, X is fluoro and R is ethyl carbonate or pivalate. In other examples, X is chloro and R is selected from isobutyrate, pivalate, or benzoate.

Disclosed herein are pharmaceutical compositions comprising a therapeutically effective amount of the compounds described herein. The composition can further comprise polyethylene glycol or any other acceptable additive.

Disclosed herein are uses of the pharmaceutical compositions described herein for the treatment of malaria, toxoplasmosis, babesiosis, coccidiosis, cryptosporidiosis, cyclosporiasis, or isosporiasis in a subject. The pharmaceutical compositions can be administered prophylactically or therapeutically. The pharmaceutical compositions can be administered to a subject with a latent infection of any of the above.

DETAILED DESCRIPTION

Figure 1:
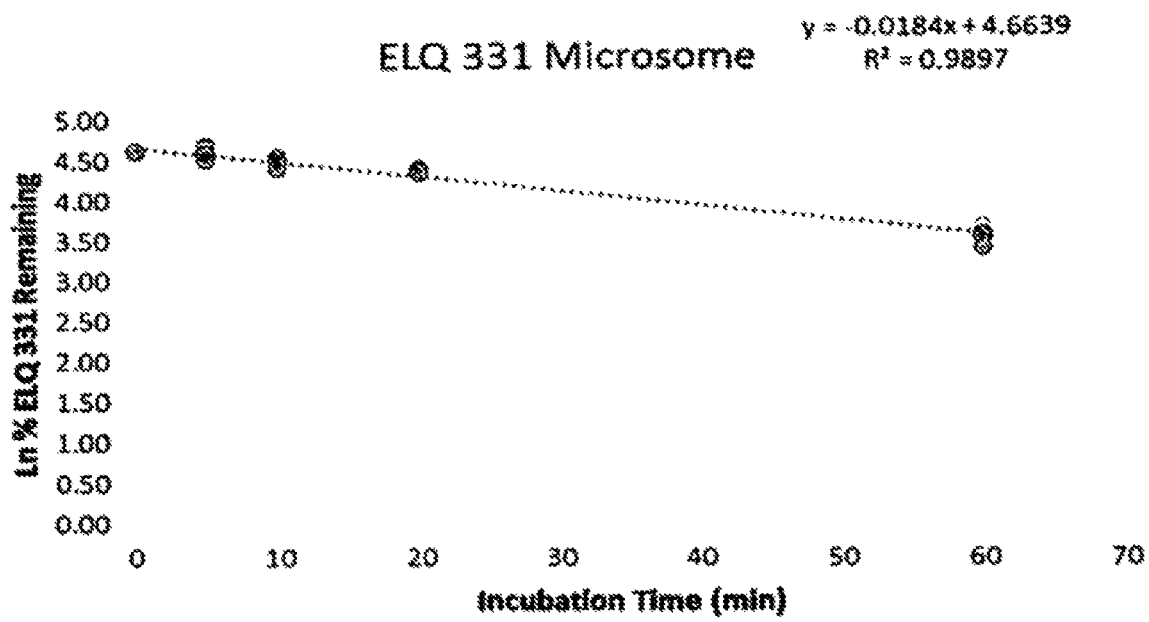
FIG. 1 is a plot of the disappearance of ELQ-331 over time in the presence of pooled human microsomes (1 mg/ml of reaction.)

Disclosed herein are ELQ-300 prodrugs comprising ester derivatives replacing the ketone group at position 4 of the ELQ-300 quinoline.

Definitions

Unless specifically defined otherwise, the technical terms, as used herein, have their normal meaning as understood in the art. The following explanations of terms and methods are provided to better describe the present compounds, compositions and methods, and to guide those of ordinary skill in the art in the practice of the present disclosure. It is also to be understood that the terminology used in the disclosure is for the purpose of describing particular embodiments and examples only and is not intended to be limiting.

As used herein, the singular terms "a," "an," and "the" include plural referents unless context clearly indicates otherwise. Similarly, the word "or" is intended to include "and" unless the context clearly indicates otherwise. Also, as

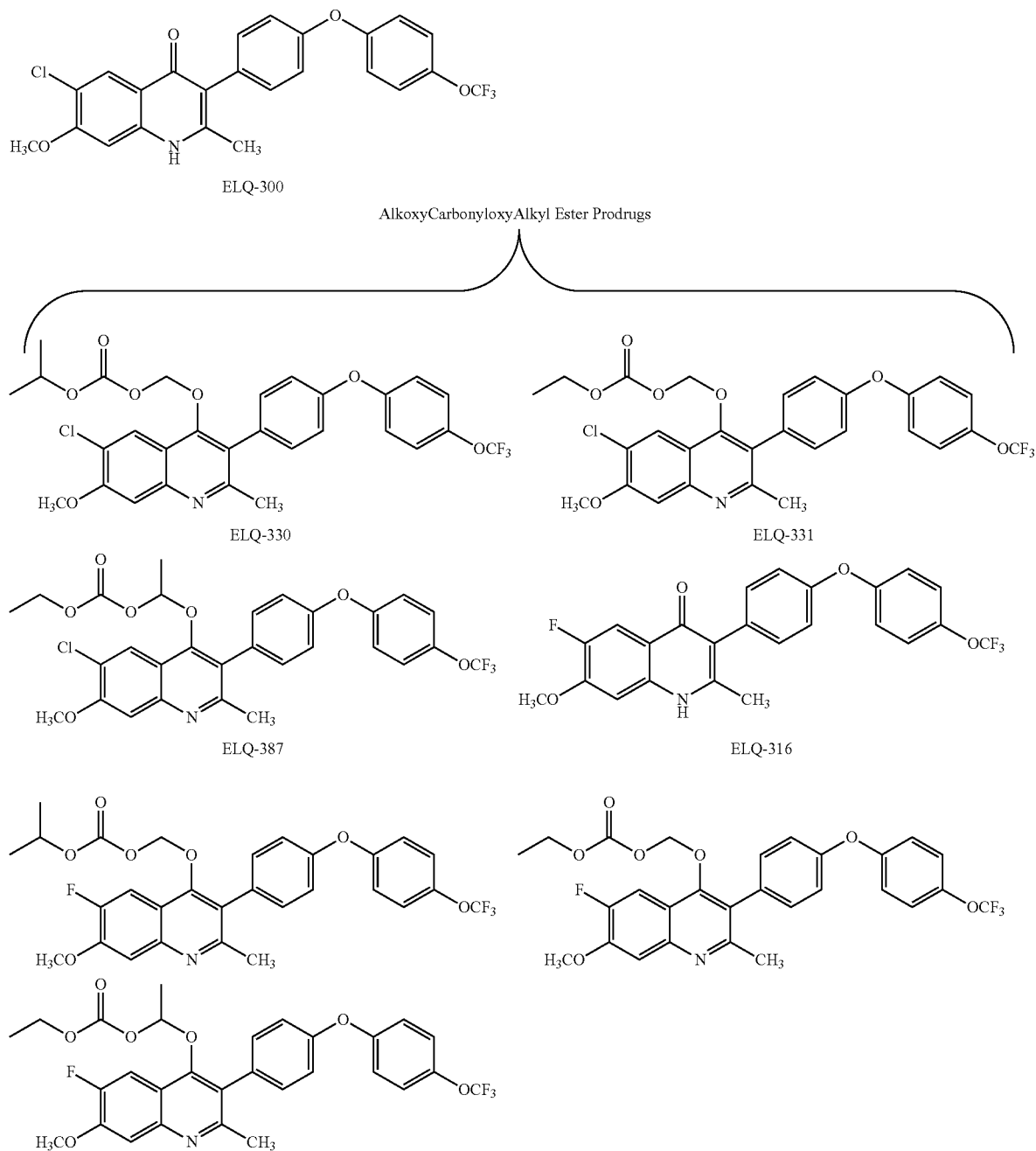

used herein, the term "comprises" means "includes." Hence "comprising A or B" means including A, B, or A and B.

"Administration of" and "administering" a compound refers to providing a compound, (such as a prodrug of a compound), or a pharmaceutical composition comprising a compound or prodrug thereof to a subject. The compound or composition can be administered by another person to the subject or it can be self-administered by the subject.

The term "alkyl" refers to a branched or unbranched saturated hydrocarbon group, such as methyl, ethyl, n-propyl, isopropyl, n-butyl, isobutyl, t-butyl, pentyl, hexyl, heptyl, octyl, decyl, tetradecyl, hexadecyl, eicosyl, tetracosyl and the like. A "lower alkyl" group is a saturated branched or unbranched hydrocarbon having from 1 to 6 carbon atoms ($C_{1-6}$alkyl). The term "alkyl" also includes cycloalkyl. The alkyl group may be a "substituted alkyl" wherein one or more hydrogen atoms are substituted with a substituent such as halogen, cycloalkyl, alkoxy, amino, hydroxyl, aryl, or carboxyl.

Alkenyl refers to an unsaturated hydrocarbon group comprising at least one carbon-carbon double bond.

The term "alkoxy" refers to an alkyl group attached to an oxygen atom to form an ether. The alkoxy group may be a "substituted alkoxy" wherein one or more hydrogen atoms are substituted with a substituent such as halogen, cycloalkyl, alkoxy, amino, hydroxyl, aryl, or carboxyl.

The term "aryl" refers to any carbon-based aromatic group including, but not limited to, benzene, naphthalene, phenyl, and oxazole. The term "aryl" also includes heteroaryl, which is defined as an aromatic group that has at least one heteroatom incorporated within the ring of the aromatic group. Examples of heteroatoms include, but are not limited to: nitrogen, oxygen, sulfur, and phosphorus. The aryl group can be substituted with one or more groups including, but not limited to, alkyl, alkynyl, alkenyl, aryl, halide, nitro, amino, ester, ether, ketone, aldehyde, hydroxy, carboxylic acid, cyano, amido, haloalkyl, haloalkoxy, or alkoxy, or the aryl group can be unsubstituted.

The term "cycloalkyl" refers to a non-aromatic carbon-based ring composed of at least three carbon atoms. Examples of cycloalkyl groups include, but are not limited to, cyclopropyl, cyclobutyl, cyclopentyl, and cyclohexyl. The term "heterocycloalkyl group" is a cycloalkyl group as defined above where at least one of the carbon atoms of the ring is substituted with a heteroatom such as nitrogen, oxygen, sulfur, or phosphorus.

"Derivative" refers to a compound or portion of a compound that is derived from or is theoretically derivable from a parent compound.

The terms "halogenated alkyl" or "haloalkyl group" refer to an alkyl group as defined above with one or more hydrogen atoms present on these groups substituted with a halogen (F, Cl, Br, I). For example, a halomethyl group is a methyl group (—$CH_3$) with one or more halogens substituted for the hydrogens. A halomethyl group may include di- and tri-substituted halogens such as a trifluoromethyl group. A halogenated ether refers to a group with one or more hydrogen atoms present on an ether, such as a methyl ether (—$OCH_3$), substituted with one or more halogens. A halogenated ether may also be termed "halomethoxy" and this general term includes mono, di- and tri-substituted halogens on the ether. For example, a trifluoromethyl ether has a formula of —$OCF_3$ and can interchangeably be referred to as "trifluoromethoxy". Similarly, a difluoromethoxy ether has the formula of —$OCHF_2$.

"Heterocycle" is a term that encompasses both heteroaryls and heterocycloalkyls. Heterocycles may be monocyclic or polycyclic rings. Exemplary heterocycles include, but are not limited to, azepinyl, aziridinyl, azetyl, azetidinyl, diazepinyl, dithiadiazinyl, dioxazepinyl, dioxolanyl, dithiazolyl—, furanyl, isooxazolyl, isothiazolyl, imidazolyl, morpholinyl, oxetanyl, oxadiazolyl, oxiranyl, oxazinyl, oxazolyl, piperazinyl, pyrazinyl,pyridazinyl, pyrimidinyl, piperidyl, piperidino, pyridyl, pyranyl, pyrazolyl, pyrrolyl, pyrrolidinyl, thiatriazolyl, tetrazolyl, thiadiazolyl, triazolyl, thiazolyl, thienyl, tetrazinyl, thiadiazinyl, triazinyl, thiazinyl, thiopyranyl, furoisoxazolyl, imidazothiazolyl, thienoisothiazolyl, thienothiazolyl, imidazopyrazolyl, cyclopentapyrazolyl, pyrrolopyrrolyl, thienothienyl, thiadiazolopyrimidinyl, thiazolothiazinyl, thiazolopyrimidinyl, thiazolopyridinyl, oxazolopyrimidinyl, oxazolopyridyl, benzoxazolyl, benzisothiazolyl, benzothiazolyl, imidazopyrazinyl, purinyl, pyrazolopyrimidinyl, imidazopyridinyl, benzimidazolyl, indazolyl, benzoxathiolyl, benzodioxolyl, benzodithiolyl, indolizinyl, indolinyl, isoindolinyl, furopyrimidinyl, furopyridyl, benzofuranyl, isobenzofuranyl, thienopyrimidinyl, thienopyridyl, benzothienyl, cyclopentaoxazinyl, cyclopentafuranyl, benzoxazinyl, benzothiazinyl, quinazolinyl, naphthyridinyl, quinolinyl, isoquinolinyl, benzopyranyl, pyridopyridazinyl and pyridopyrimidinyl groups.

The terms "treatment", "treat" and "treating" refer to a therapeutic intervention that ameliorates a sign or symptom of a disease or pathological condition. As used herein, the terms "treatment", "treat" and "treating," with reference to a disease, pathological condition or symptom, also refers to any observable beneficial effect of the treatment. The beneficial effect can be evidenced, for example, a reduction in severity of some or all clinical symptoms of the disease, a slower progression of the disease, a reduction in the number of relapses of the disease, an improvement in the overall health or well-being of the subject, or by other parameters well known in the art that are specific to the particular disease.

A "prophylactic" treatment is a treatment administered to a subject who does not exhibit signs of a disease or exhibits only early signs, for the purpose of decreasing the risk of developing pathology.

A "therapeutic" treatment is a treatment administered to a subject who has already begun to exhibit signs of a disease for the purpose of slowing or reversing the pathology.

"Coadminister" means that each of at least two compounds are administered during a time frame wherein the respective periods of biological activity overlap. Thus, the term includes sequential as well as coextensive administration of two or more drug compounds.

The terms "pharmaceutically acceptable salt" or "pharmacologically acceptable salt" refers to salts prepared by conventional methods, and include basic salts of inorganic and organic acids, such as hydrochloric acid, hydrobromic acid, sulfuric acid, phosphoric acid, methanesulfonic acid, ethanesulfonic acid, malic acid, acetic acid, oxalic acid, tartaric acid, citric acid, lactic acid, fumaric acid, succinic acid, maleic acid, salicylic acid, benzoic acid, phenylacetic acid, and mandelic acid.

Pharmaceutically acceptable salts of the presently disclosed compounds also include those formed from cations such as sodium, potassium, aluminum, calcium, lithium, magnesium, zinc, and from bases such as ammonia, ethylenediamine, N-methyl-glutamine, lysine, arginine, ornithine, choline, N,N'-dibenzylethylenediamine, chloroprocaine, diethanolamine, procaine, N-benzylphenethylamine, diethylamine, piperazine, tris(hydroxymethyl)aminomethane, and tetramethylammonium hydroxide. These salts may be prepared by standard procedures, for example by reaction of the free acid with a suitable organic or inorganic base. Any chemical compound recited in this specification may alternatively be administered as a pharmaceutically acceptable salt thereof.

Pharmaceutically acceptable salts are also inclusive of the free acid, base, and zwitterionic forms. Descriptions of exemplary pharmaceutically acceptable salts can be found in Stahl and Wermuth, Eds., Handbook of Pharmaceutical Salts; Properties, Selection and Use, Wiley VCH (2008). When compounds disclosed herein include an acidic function such as a carboxy group, then suitable pharmaceutically acceptable cation pairs for the carboxy group are well known to those skilled in the art and include alkaline, alkaline earth, ammonium, and quaternary ammonium cations. Such salts are known to those of skill in the art. For additional examples of "pharmacologically acceptable salts," see Berge et al., J. Pharm. Sci. 66:1 (1977).

The term "subject" includes both human and veterinary subjects.

A "therapeutically effective amount" refers to a quantity of a specified agent sufficient to achieve a desired effect in a subject being treated with that agent. For example, this may be the amount of a compound disclosed herein useful in treating malaria in a subject. Ideally, a therapeutically effective amount of an agent is an amount sufficient to inhibit or treat the disease without causing substantial toxicity in the subject. The therapeutically effective amount of an agent will be dependent on the subject being treated, the severity of the affliction, and the manner of administration of the therapeutic composition. Methods of determining a therapeutically effective amount of the disclosed compound sufficient to achieve a desired effect in a subject infected with a malaria parasite will be understood by those of skill in the art in light of this disclosure.

The synthesis processes described herein can be monitored according to any suitable method known in the art. For example, product formation can be monitored by spectroscopy, such as nuclear magnetic resonance spectroscopy (e.g., $^1$H or $^{13}$C NMR), infrared spectroscopy, spectrophotometry (e.g., UV-visible), mass spectrometry, or by chromatography such as high performance liquid chromatograpy (HPLC) or thin layer chromatography.

Earlier attempts to develop a prodrug of ELQ-300 were unsuccessful—the prodrugs proved to be too unstable in physiological media to result in sufficient bioavailability or too stable to be metabolized into active ELQ-300. For example, the 4-position acetyl ester (ELQ-370) is chemically unstable to mildly acidic conditions and even decomposes rapidly in methanol while the corresponding 4-oxo linked dimethylcarbamate analog (ELQ-301) is stable to metabolism and displays inferior in vivo efficacy compared to the parent compound ELQ-300.

Synthesis of ELQ-300 Carbonate Esters

Disclosed herein are O-linked esters and carbonates that are effective prodrugs of ELQ-300. ELQ-337 is the O-linked ethyl-carbonate of ELQ-300. O-linked carbonate esters of ELQs enhance oral delivery and efficacy against murine malaria. Placement of the promoiety at the 4-oxo-position removes the H-atom from the ring nitrogen thereby upsetting crystal lattice formation. This is evidenced by a reduction of the melting point from 314° C. for ELQ-300 to 160° C. for ELQ-337.

ELQ-337 is produced from ELQ-300 in one step, using sodium hydride in tetrahydrofuran. Ethyl chloroformate is then added dropwise. The reaction goes to completion in minutes upon the addition of the chloroformate forming one regioisomer in very high yield. ELQ-337 is chemically stable in 50/50 mixtures of methanol and water at pH 3 and 8 overnight. Results are summarized in Scheme 1

Scheme 1

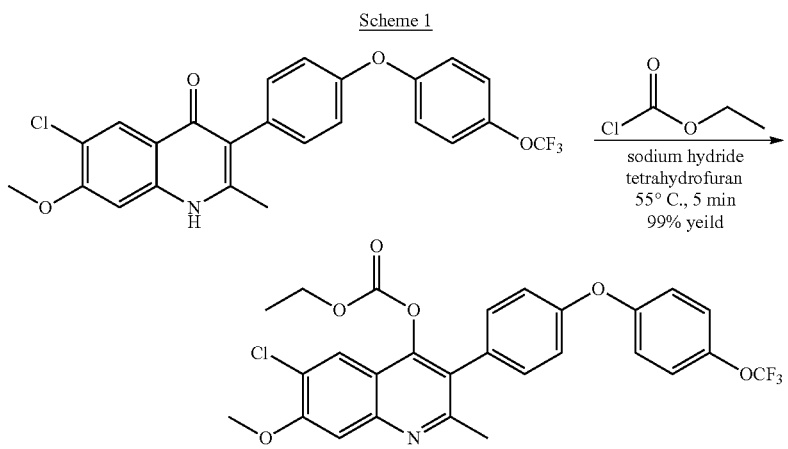

Synthesis of ELQ-300 Prodrugs

The term "prodrug" refers to any active or inactive compound that is modified chemically through an in vivo physiological action, such as hydrolysis or metabolism, into an active compound following administration of the prodrug to a subject. The suitability and techniques involved in making and using prodrugs are well known by those skilled in the art. For a general discussion of prodrugs involving esters see Svensson and Tunek, *Drug Metabolism Reviews* 165 (1988), and Bundgaard, Design of Prodrugs, Elsevier (1985).

Ester derivatives of ELQ-300, including carbonate esters are disclosed.

Ester Formation:

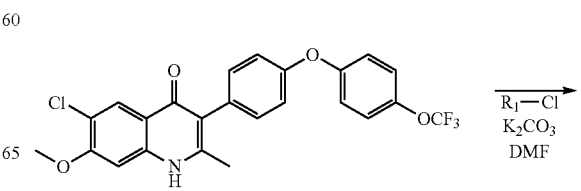

-continued

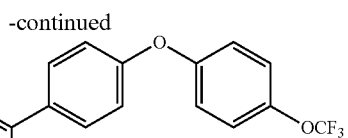

The R₁ group selected can result in the formation of any ester. Esters generally have the structure:

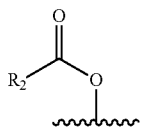

Carbonate Esters Generally have the Structure:

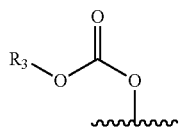

wherein $R_2$ or $R_3$ can be any alkyl, substituted alkyl, alkenyl, substituted alkenyl, ether, substituted ether, aryl, substituted aryl, heterocycloalkyl, substituted heterocycloalkyl, heteroaryl, or substituted heteroaryl.

The compounds disclosed herein have the general structure of Formula I:

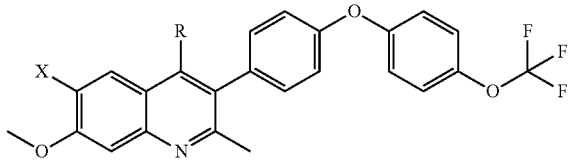

wherein X is halo and R is ester. In particular examples X is chloro or fluoro. In still other examples, R is a carbonate ester. The carbonate can be any carbonate ester including ethyl carbonate; 2-methoxyethylcarbonate; 2-(2-methoxyethoxy)ethyl carbonate; 2-(2-(2-methoxyethoxy)ethoxy)ethyl) carbonate; allyl carbonate; tert-butyl carbonate; ((2,2-dimethyl-1,3-dioxolan-4-yl)methyl) carbonate; ((2-oxo-1,3-dioxolan-4-yl)methyl carbonate; and 2,3-dihydroxypropyl carbonate. In still further examples, R is a non-carbonate ester. The non-carbonate ester can be any non-carbonate ester including isobutyrate, pivalate, and benzoate groups.

As described herein, the definition of ester, particularly with regard to the R group of Formula I above does not encompass carbamates. Carbamates have the general structure:

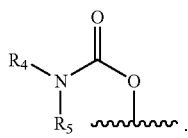

Pharmaceutical Compositions

The compounds disclosed herein may be included in pharmaceutical compositions (including therapeutic and prophylactic formulations). Pharmaceutical compositions as described herein include one or more compounds according to the present description. In addition to one or more compounds as described herein, pharmaceutical compositions according to the present disclosure may include one or more additional therapeutic agents, including, for example, one or more additional antimalarial or anti-infective agents, antibiotics, anti-inflammatory agents, or drugs that are used to reduce pruritus, such as an antihistamine. In preparing the pharmaceutical compositions, the one or more compounds as described herein and, optionally, the one or more additional active agents, may be combined together with one or more pharmaceutically acceptable vehicles, salts, solubilizing agents (e.g., co-crystals, lipids, or hydrophilic polymers) or carriers. The pharmaceutical compositions described herein may be combined with or used simultaneously with one or more other therapeutic regimens or compositions. Where one or more additional antimalarial or anti-infective agent is included in a pharmaceutical composition according to the present invention, such agent(s) may be selected from, for example, quinolines, such as chloroquine, quinine, and mefloquine; the antifolates, such as pyrimethamine and sulfadoxine; the anti-respiratory agents atovaquone and/or proguanil, as well as inhibitors of parasite dihydro-orotate dehydrogenase (DHOD) such as DSM265.

Pharmaceutical compositions according to the present invention can be administered to subjects by a variety of mucosal administration modes, including by oral, rectal, intranasal, intrapulmonary, or transdermal delivery, or by topical delivery to other surfaces. Optionally, the compositions can be administered by non-mucosal routes, including by intramuscular, subcutaneous, intravenous, intra-arterial, intra-articular, intraperitoneal, intrathecal, intracerebroventricular, or parenteral routes. In an embodiment, the compound can be administered ex vivo by direct exposure to cells, tissues or organs originating from a subject. To formulate the pharmaceutical compositions, the one or more compounds can be combined with various pharmaceutically acceptable additives, as well as a base or vehicle for dispersion of the compound. Such additives include, but are not limited to, pH control agents, such as arginine, sodium hydroxide, glycine, hydrochloric acid, and citric acid. In addition, local anesthetics (for example, benzyl alcohol), isotonizing agents (for example, sodium chloride, mannitol, sorbitol), adsorption inhibitors (for example, Tween 80 or medium chain triacylglycerols such as myglyol 812), solubility enhancing agents (for example, cyclodextrins and derivatives thereof), stabilizers (for example, serum albumin), and reducing agents (for example, glutathione) can be included.

In preparing a pharmaceutical composition according to the present description, the one or more compounds can be dispersed in a base or vehicle which can include a hydrophilic compound having a capacity to disperse the disclosed compound and any additives. The base can be selected from a wide range of suitable compounds, including but not limited to, copolymers of polycarboxylic acids or salts thereof; carboxylic anhydrides (for example, maleic anhydride); with other monomers (for example, methyl(meth) acrylate and acrylic acid); hydrophilic vinyl polymers, such as polyvinyl acetate, polyvinyl alcohol, polyvinylpyrrolidone, cellulose derivatives such as hydroxymethylcellulose and hydroxypropylcellulose; natural polymers, such as chitosan, collagen, sodium alginate, gelatin, hyaluronic acid; and nontoxic metal salts thereof.

A biodegradable polymer may be selected as a base or vehicle, such as, for example, polylactic acid, poly(lactic acid-glycolic acid) copolymer, polyhydroxybutyric acid, poly(hydroxybutyric acid-glycolic acid) copolymer and mixtures thereof. Alternatively or additionally, synthetic fatty acid esters such as polyglycerin fatty acid esters and sucrose fatty acid esters may be employed as vehicles. Hydrophilic polymers and other vehicles can be used alone or in combination, and enhanced structural integrity can be imparted to the vehicle by, for example, partial crystallization, ionic bonding, or cross-linking. The vehicle may be provided in a variety of forms, including fluid or viscous solutions, gels, pastes, powders, microspheres, and films for direct application to a mucosal surface.

The one or more compounds may be combined with the base or vehicle according to a variety of methods, and release of the compound can be via diffusion, disintegration of the vehicle, or associated formation of water channels. In some embodiments, the compound can be dispersed in microcapsules (microspheres) or nanoparticles prepared from a suitable polymer, for example, 5-isobutyl-2-cyanoacrylate (see, for example, Michael et al, *J. Pharmacy Pharmacol* 43, 1-5, 1991), and dispersed in a biocompatible dispersing medium, which may provide sustained delivery and biological activity over a protracted time.

In certain embodiments, the pharmaceutical compositions of the disclosure can contain as pharmaceutically acceptable vehicles, substances as required to approximate physiological conditions, such as pH adjusting and buffering agents, tonicity adjusting agents, and wetting agents, for example, sodium acetate, sodium lactate, sodium chloride, potassium chloride, calcium chloride, sorbitan monolaurate, and triethanolamine oleate.

For solid compositions, conventional nontoxic pharmaceutically acceptable vehicles may be used which include, for example, pharmaceutical grades of mannitol, lactose, starch, magnesium stearate, sodium saccharin, talcum, cellulose, glucose, sucrose, and magnesium carbonate.

Pharmaceutical compositions for administering the one or more compounds can also be formulated as a solution, microemulsion, or other ordered structure suitable for a high concentration of active ingredients. The vehicle may be a solvent or dispersion medium containing, for example, water, ethanol, polyol (for example, glycerol, propylene glycol, and liquid polyethylene glycol), and suitable mixtures thereof. Proper fluidity for solutions may be maintained, for example, by the use of a coating such as lecithin, by the maintenance of a desired particle size in the case of dispersible formulations, and by the use of surfactants.

In an embodiment, it may be desirable to include isotonic agents, for example, sugars, polyalcohols such as mannitol and sorbitol, or sodium chloride in the composition. Prolonged absorption of the one or more compounds may be obtained by including in the composition an agent which delays absorption, for example, monostearate salts and gelatin.

In certain embodiments, the one or more compounds can be administered in a time release formulation, for example in a composition which includes a slow release polymer. These compositions may be prepared with vehicles that will protect against rapid release, for example, a controlled release vehicle such as a polymer, microencapsulated delivery system or bioadhesive gel. Controlled release binders suitable for use in accordance with the disclosure include any biocompatible controlled release material which is inert to the active agent and which is capable of incorporating the compound and/or other biologically active agent. Numerous such materials are known in the art. Controlled-release binders may be materials that are metabolized slowly under physiological conditions following their delivery (for example, at a mucosal surface, or in the presence of bodily fluids).

Exemplary binders include, but are not limited to, biocompatible polymers and copolymers well known in the art for use in sustained release formulations. Such biocompatible compounds are non-toxic and inert to surrounding tissues, and do not trigger significant adverse side effects, such as nasal irritation, immune response, or inflammation. They are metabolized into metabolic products that are also biocompatible and easily eliminated from the body.

Exemplary polymeric materials for use in the present disclosure include, but are not limited to, polymeric matrices derived from copolymeric and homopolymeric polyesters having hydrolyzable ester linkages. A number of these are known in the art to be biodegradable and to lead to degradation products having no or low toxicity.

Exemplary polymers include polyglycolic acids and polylactic acids, poly(DL-lactic acid-co-glycolic acid), poly(D-lactic acid-co-glycolic acid), and poly(L-lactic acid-coglycolic acid). Other useful biodegradable or bioerodable polymers include, but are not limited to, poly(epsilon-caprolactone), poly(epsilon-caprolactone-CO-lactic acid), poly(epsilon-caprolactone-CO-glycolic acid), poly(beta-hydroxy butyric acid), poly(alkyl-2-cyanoacrylate), hydrogels such as poly(hydroxyethyl methacrylate), polyamides, poly (amino acids) such as L-leucine, glutamic acid, L-aspartic acid, poly(ester urea), poly(2-hydroxyethyl DL-aspartamide), polyacetal polymers, polyorthoesters, polycarbonate, polymaleamides, polysaccharides, and copolymers thereof.

Methods for preparing such formulations are well known to those skilled in the art (see, for example, *Sustained and Controlled Release Drug Delivery Systems*, J. R. Robinson, ed., Marcel Dekker, Inc., New York, 1978). Other useful formulations include controlled-release microcapsules (U.S. Pat. Nos. 4,652,441 and 4,917,893), lactic acid-glycolic acid copolymers useful in making microcapsules and other formulations (U.S. Pat. Nos. 4,677,191 and 4,728,721) and sustained release compositions for water-soluble peptides (U.S. Pat. No. 4,675,189).

The pharmaceutical compositions of the disclosure typically are sterile and stable under conditions of manufacture, storage and use. Sterile solutions can be prepared by incorporating the compound in the required amount in an appropriate solvent with one or a combination of ingredients enumerated herein, as required, followed by filtered sterilization. Dispersions may be prepared by incorporating the compound and/or other biologically active agent into a sterile vehicle that contains a basic dispersion medium and the required other ingredients from those enumerated herein. In the case of sterile powders, methods of preparation include vacuum drying and freeze-drying which yields a powder of the compound plus any additional desired ingredient from a previously sterile-filtered solution thereof. The prevention of the action of microorganisms can be accomplished by various antibacterial and antifungal agents, for example, parabens, chlorobutanol, phenol, sorbic acid, and thimerosal.

Methods of Treatment

The compounds and pharmaceutical compositions disclosed herein can be used for treating, inhibiting or preventing parasitic diseases, such as malaria, caused by organisms such as *Plasmodium* sp., including *Plasmodium falciparum*. Other examples of human or animal parasitic diseases that may be treated using the compounds and pharmaceutical compositions disclosed herein include toxoplasmosis, amebiasis, giardiasis, leishmaniasis, trypanosomiasis, coccidiosis, and schistosomiasis, caused by organisms such as *Toxoplasma* sp., *Eimeria* sp., *Babesia* sp, or *Theileria* sp. Additional parasites that cause malaria include *Plasmodium vivax, Plasmodium ovale, Plasmodium knowlesi, Plasmodium malariae, Plasmodium yoelii*, and *Plasmodium berghei*.

In particular embodiments, the compounds and compositions disclosed herein can be administered to a subject to prevent or inhibit drug-resistant malaria such as chloroquine-resistant malaria or multidrug-resistant malaria that is caused by organisms harboring resistance to chloroquine, quinine, mefloquine, pyrimethamine, dapsone, atovaquone, *P. falciparum* DHOD inhibitors such as DSM265 (Coteron J M et al, *J Med Chem* 54, 5540-5561 (2011); incorporated by reference herein) or any other available anti-malarial drug.

In further embodiments, the compounds and pharmaceutical compositions disclosed herein can be coadministered with another pharmaceutically active compound. For example, the compounds may be coadministered with quinine, chloroquine, atovaquone, proguanil, primaquine, amodiaquine, mefloquine, piperaquine, artemisinin, artesunate, endoperoxidases, methylene blue, pyrimethamine, sulfadoxine, artemether-lumefantrine (Coartem®), dapsone-chlorproguanil (LAPDAP®), artesunate, quinidine, clopidol, pyridine/pyridinol analogs, 4(1H)-quinolone analogs, dihydroartemisinin, a mixture of atovaquone, proguanil, an endoperoxide, an acridone as disclosed in WO 2008/064011, another 3-aryl quinoline as disclosed in WO 2010/059633, or any combination or mixtures of these, whether administered separately or in a single pharmaceutical composition.

In accordance with the various treatment methods of the disclosure, the compound can be delivered to a subject in a manner consistent with conventional methodologies associated with management of the disorder for which treatment or prevention is sought. In accordance with the disclosure herein, a prophylactically or therapeutically effective amount of the compound and/or other biologically active agent is administered to a subject in need of such treatment for a time and under conditions sufficient to prevent, inhibit, and/or ameliorate a selected disease or condition or one or more symptom(s) thereof.

Typical subjects intended for treatment with the compounds, compositions and methods of the present disclosure include humans, as well as non-human primates and other animals such as companion animals, livestock animals, animals used in models of parasitic infection, or animals used in pharmaceutical testing, such as pharmacokinetics and toxicological testing, including mice, rats, rabbits, and guinea pigs.

To identify subjects for prophylaxis or treatment according to the methods of the disclosure, accepted screening methods are employed to determine risk factors associated with a parasitic infection to determine the status of an existing disease or condition in a subject. These screening methods include, for example, preparation of a blood smear from an individual suspected of having malaria. The blood smear is then fixed in methanol and stained with Giemsa and examined microscopically for the presence of *Plasmodium* infected red blood cells. These and other routine methods allow a clinician to select patients in need of therapy using the methods and pharmaceutical compositions of the disclosure.

The administration of the disclosed compounds and pharmaceutical compositions can be for prophylactic or therapeutic purposes or to block transmission of disease. When provided prophylactically, the compound is administered to a subject in advance of a symptom. The prophylactic administration of the compound serves to prevent or ameliorate subsequent disease process or to achieve disease eradication. When provided therapeutically, the compound is administered to a subject at or after the onset of a symptom of disease or infection.

For prophylactic and therapeutic purposes, the compound or pharmaceutical composition may be administered to the subject orally or in a single bolus delivery, via continuous delivery (for example, continuous transdermal, mucosal or intravenous delivery) over an extended time period, or in a repeated administration protocol (for example, by an hourly, daily or weekly, repeated administration protocol). The therapeutically effective dosage of the compound may be provided as repeated doses within a prolonged prophylaxis or treatment regimen to yield clinically significant results to alleviate one or more symptoms or detectable conditions associated with a targeted disease or condition as set forth herein.

Determination of effective dosages in this context may be based on animal model studies followed up by human clinical trials and may be guided by administration protocols that significantly reduce the occurrence or severity of targeted disease symptoms or conditions in the subject. Suitable models in this regard include, for example, murine, rat, avian, porcine, feline, non-human primate, and other accepted animal model subjects known in the art. Alternatively, effective dosages may be determined using in vitro models (for example, immunologic and histopathologic assays). Using such models, calculations and adjustments can be required to determine an appropriate concentration and dose to administer a therapeutically effective amount of the compound (for example, amounts that are effective to elicit a desired immune response or alleviate one or more symptoms of a targeted disease). In certain embodiments, an effective amount or effective dose of the compound may simply inhibit or enhance one or more selected biological activities correlated with a disease or condition, as set forth herein, for either therapeutic or diagnostic purposes.

The actual dosage of the compound may vary according to factors such as the disease indication and particular status of the subject (for example, the subject's age, size, fitness, extent of symptoms, and susceptibility factors), time and route of administration, other drugs or treatments being administered concurrently, as well as the specific pharmacology of the compound for eliciting the desired activity or biological response in the subject. Dosage regimens can be adjusted to provide an optimum prophylactic or therapeutic response.

A therapeutically effective amount may be one in which any toxic or detrimental side effects of the compound and/or other biologically active agent is outweighed in clinical terms by therapeutically beneficial effects. A non-limiting range for a therapeutically effective amount of a compound and/or other biologically active agent within the methods and compositions of the disclosure is about 0.01 mg/kg body weight to about 100 mg/kg body weight, such as about 0.05 mg/kg to about 50 mg/kg body weight, or about 0.5 mg/kg to about 5 mg/kg body weight.

The dosage may be varied to maintain a desired concentration at a target site (for example, the lungs or systemic circulation). Higher or lower concentrations can be selected based on the mode of delivery, for example, trans-epidermal, rectal, oral, pulmonary, or intranasal delivery versus intravenous or subcutaneous delivery. Dosage can also be adjusted based on the release rate of the administered formulation, for example, of an intrapulmonary spray versus powder or sustained release oral versus injected particulate or transdermal delivery formulations.

The instant disclosure also includes kits, packages and multi-container units containing the herein described pharmaceutical compositions, active ingredients, and/or devices and consumables that facilitate the administration the same for use in the prevention and treatment of diseases and other conditions in mammalian subjects.

In an embodiment, the compound may be formulated in a pharmaceutical composition for delivery to a subject. In such embodiments, pharmaceutical compositions according to the present description may be used. The compound or composition within which it is formulated may be contained in a bulk dispensing container or unit or multiunit dosage form. Optional dispensers can be provided, for example, a pulmonary or intranasal spray applicator. Packaging materials optionally include a label or instruction indicating for what treatment purposes and/or in what manner the pharmaceutical agent packaged therewith can be used.

In an embodiment, the method of treating a *Plasmodium* infection comprises administering a therapeutically effective amount of a compound. The compound may be administered orally, subcutaneously, intravenously, or intramuscularly to a subject suffering from or at risk of suffering from a *Plasmodium* infection.

Mechanism of Action of ELQ-300 Prodrugs

The chemical structures of the prodrugs ELQ-330 and ELQ-331 are shown in Scheme 1 below along with the structure of the parent drug ELQ-300. It is well established that alkoxycarbonyloxyalkyl ester prodrugs serve as neutral lipophilic prodrugs of pharmaceutical agents. Consider for example the clinical drug Tenofovir Disoproxil (FIG. 2) which contains two alkoxycarbonyloxyalkyl ester promoieties attached to a central phosphonate residue. ELQ-330 and ELQ-331 were formed by reaction of ELQ-300 with either chloro-methyl-isopropylcarbonate (ELQ-330) or chloro-methyl-ethylcarbonate (ELQ-331).

The development of ELQ-300 for clinical use is hindered by relatively poor water solubility that is linked to a high degree of crystallinity. One simple measure that can be used to compare crystal lattice strength is the melting point. Pure ELQ-300 has a melting point of >300° C. Disclosed herein are compounds with an alkoxycarbonate ester at position 4 of the quinoline ring system have significantly reduced crystal lattice energy compared to ELQ-300 as evidenced by an impressive drop in the melting point: 99.7-99.9/ELQ-330; 103.5-103.7° C./ELQ-331; and 135.0-135.7° C./ELQ-387. Without being bound by theory, reducing crystallinity means that the alkoxycarbonate ester prodrugs can have a reduced tendency for re-crystallization in the intestines prior to absorption. As a consequence, this subclass of ELQ prodrugs, i.e., the alkoxycarbonate esters, can be used to improve oral bioavailability and bloodstream exposures to the active parent ELQs (e.g., ELQ-271, ELQ-300, ELQ-316, and ELQ-400).

Figure 2:
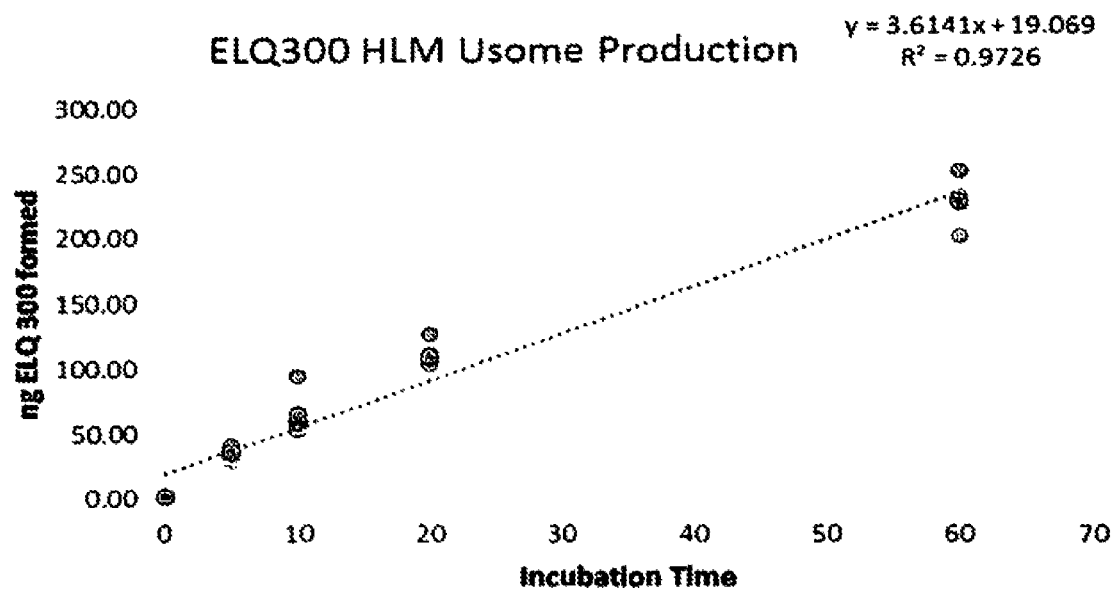
FIG. 2 is a plot of the conversion of ELQ-331 to ELQ-300 in the presence of pooled human microsomes. The presence or absence of NADPH did not affect the conversion rate.

The potential for hepatic P450-dependent metabolism of ELQ-331 at 11 μM was assessed using pooled human liver microsomes in the presence of an NADPH regenerating system. The loss of substrate was monitored by LC/MS/MS. Midazolam was monitored as a well characterized positive control. Midazolam represents a drug with comparatively low metabolic stability. Incubations were conducted in the absence of the NADPH regenerating system to monitor for potential P450-independent metabolism. In the absence of NADPH we did not observe significant metabolism of the midazolam control however it was rapidly metabolized in the presence of NADPH with a t112 value of 2.6 minutes. In the presence of 1 mg/ml of pooled human microsomes and NADPH regenerating system we observed a linear conversion of ELQ-331 to ELQ-300 throughout the first 20 minutes of reaction time. The $t_{1/2}$ value recorded for ELQ-331 was 37.7 minutes in the presence or absence of NADPH. That the conversion rate of the prodrug ELQ-331⇒ELQ-300 did not vary between the samples with and without NADPH indicates that host esterases are primarily responsible for enzymatic production of ELQ-300 from ELQ-331 (FIGS. 1 and 2)

EXAMPLES

The following examples are for illustration only. In light of this disclosure, those of skill in the art will recognize that Scheme 1:

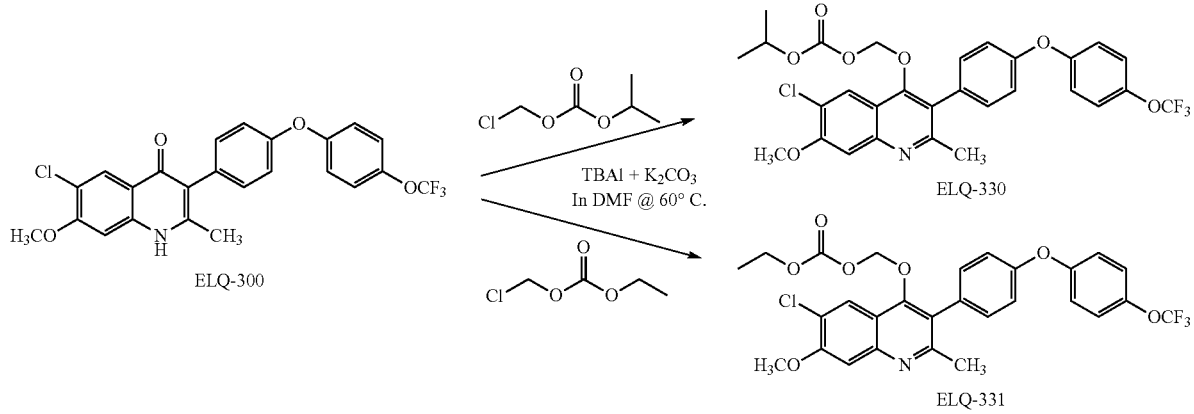

variations of these examples and other examples of the disclosed invention be possible without undue experimentation.

Example 1—ELQ-331 Synthesis

ELQ-300 (0.85 g, 1.8 mmol), tetrabutylammonium iodide (1.33 g, 3.6 mmol) and potassium carbonate (0.50 g, 3.6 mmol) were dissolved anhydrous dimethylformamide (8 ml) in a flame-dried round bottom flask at 60° C. under inert atmosphere. Chloromethyl ethyl carbonate (0.5 g, 3.6 mmol) was added dropwise and the reaction stirred under inert atmosphere at 60° C. for two hours, at which point reaction completion was confirmed by thin layer chromatography. After cooling to room temperature, the reaction solvent was removed under reduced pressure and the mixture taken up in water (10 ml) and extracted with dichloromethane (3×20 ml). Combined organic layers were washed with brine (10 ml), dried over $MgSO_4$, and the dichloromethane evaporated under reduced pressure. The resulting crude product was purified by flash chromatography (EtOAc/DCM) to yield the title compound, ELQ-331, as a white crystalline solid (560 mg, 54%). $^1$H NMR (400 MHz, DMSO-$d_6$): δ=7.98 (s, 1H), 7.57 (s, 1H), 7.44 (m, 4H), 7.21 (m, 4H), 5.76 (s, 2H), 5.35 (s, 2H), 4.03 (s, 3H), 2.44 (s, 3H), 1.11 (t, 3H, J=7.1 Hz); M.P. (° C.): 103.5-103.7.

Example 2—Characterization of ELQ-331 by Gas Chromatography-Mass Spectrometry (Gc-Ms)

ELQ-331 was characterized by gc-ms on an Agilent 5977A MSD/5890B gas chromatography system. The instrument was equipped with an Agilent J&W GC column with stationary phase HP-5MS with overall dimensions of 30 m×0.250 mm×0.25 micrometers with helium as the inert carrier gas. The temperature gradient was 200-300° C. at 30° C./min.

Example 3—ELQ-387 Synthesis

Tetrabutyl-ammonium iodide (0.15 g, 0.42 mmol), potassium carbonate (0.06 g, 0.42 mmol), and 1-chloroethyl ethyl carbonate (0.06 mL, 0.42 mmol) were dissolved in anhydrous dimethylformamide (5 mL) in a flame-dried round bottom flask at 70° C. under inert atmosphere. ELQ-300 (0.10 g, 0.21 mmol) was added and the reaction stirred under inert atmosphere at 70° C. for four hours, until complete by thin layer chromatography. The reaction was cooled to room temperature and the reaction solvent evaporated under temperature and the reaction solvent evaporated under reduced pressure. The mixture was taken up in water (10 ml) and extracted with dichloromethane (3×15 mL). Combined organic layers were washed with brine (15 mL) and concentrated. Purification by silica column chromatography (EtOAc/DCM) yielded the title compound, ELQ-387, as a white crystalline solid (39 mg, 32%). $^1$H NMR (400 MHz, DMSO-$d_6$): δ=8.03 (s, 1H), 7.54 (s, 1H), 7.44 (m, 3H), 7.25 (m, 2H), 7.20 (m, 2H), 5.83 (q, 1H, J=5.4 Hz), 4.02 (s, 3H), 3.79 (m, 2H), 2.44 (s, 3H), 1.19 (d, 3H, J=5.3 Hz), 0.88 (t, 3H, J=7.1 Hz); M.P. (° C.): 135.0-135.7.

Example 4—In Vitro Antlplasmodial Activity of ELQ-330, ELQ-331, and ELQ-387 vs. Chloroquine Sensitive (D6) and Resistant (Dd2, Tm90.C2B) Strains of *Plasmodium falciparum*

ELQ-330, ELQ-331 and ELQ-387 were evaluated for anti-plasmodial activity by the fluorescence based SYBR green assay developed in our lab and published in 2004. Briefly, experiments were set up in triplicate in 96-well plates (Costar, Corning) with 2-fold dilutions of each drug across the plate in a total volume of 100 μL and at a final red blood cell concentration of 2% (v/v). The dilution series was initiated at a concentration of 1 μM and the experiment was repeated beginning with a lower initial concentration for those compounds in which the $IC_{50}$ value was below 10 nM. Automated pipetting and dilution was carried out with the aid of a programmable Precision 2000 robotic station (BioTek, Winooski, Vt.). An initial parasitemia of 0.2% was obtained by addition of normal uninfected red cells to a stock culture of asynchronous parasite infected red cells (PRBC). The plates were incubated for 72 h at 37° C. in an atmosphere of 5% $CO_2$, 5% $O_2$, and 90% $N_2$. After this period, the SYBR Green I dye-detergent mixture (1 00 !JL) was added and the plates were incubated at room temperature for an hour in the dark and then placed in a 96-well fluorescence plate reader (Spectramax Gemini-EM, Molecular Diagnostics) for analysis, with excitation and emission wavelength bands centered at 497 and 520 nm, respectively. The fluorescence readings were plotted against the logarithm of the drug concentration, and curve fitting by nonlinear regression analysis (GraphPad Prism software) yielded the drug concentration that produced 50% of the observed decline relative to the maximum readings in drug-free control wells ($IC_{50}$). Chloroquine was used as an internal control to establish zero percent viability and cross-resistance.

$IC_{50}$ values are presented in Table 1. As shown the $IC_{50}$ values for alkoxycarbonyloxyalkyl ester prodrugs ELQ-330 and ELQ-387 are significantly higher than for the parent molecule ELQ-300 against all three tested strains. These results indicate that while *P. falciparum* infected red cells apparently have the enzymic capacity to break down the prodrugs to release ELQ-300 it would appear that for these alkoxycarbonyloxyalkyl ester are poorly processed by parasite encoded esterases. It is both interesting and significant that the $IC_{50}$ values for ELQ-331 are quite similar to the ELQ-300 values, thereby indicating that this prodrug is more effectively converted to ELQ-300 by *P. falciparum* esterases. Taken together and because it appears that ELQ-331 is more efficiently converted to ELQ-300 by both host as well as parasite esterases we hypothesized that this drug would have superior efficacy in vivo.

TABLE 1

Antiplasmodial activities for standard antimalarials (Chloroquine and Atovaquone) and ELQ-300 and the esterase sensitive prodrugs ELQ-330, ELQ-331, and ELQ-387 against drug sensitive (06) and multidrug resistant (Dd2 and Tm90:C2B) strains of *P. falciparum*.

| Drug | $IC_{50}$, nM, *P. falciparum* strain D6[a] | $IC_{50}$, nM, *P. falciparum* strain Dd2[a] | $IC_{50}$, nM, *P. falciparum* strain Tm90-C2B[a] |
|---|---|---|---|
| Chloroquine | 10 | 137 | 98 |
| Atovaquone | 0.2 | 0.2 | >250 |
| ELQ-300 | 6 | 6 | 2 |
| ELQ-330 | 62 | 38 | 47 |
| ELQ-331 | 6 | 8 | 4 |
| ELQ-387 | 326 | 141 | 231 |

[a]$IC_{50}$ = The drug concentration that decreases parasite proliferation by 50% relative to control (no-drug) values. D6 is sensitive to chloroquine while Dd2 and Tm90-C2B are resistant to chloroquine. Tm90-C2B Is also resistant to the antirespiratory drug atovaquone.

Example 5—In Vivo Efficacy of Alkoxycarbonyloxyalkyl Ester Prodrugs ELQ-330 and ELQ-331 Against the Blood Stage of Murine Malaria Infection Typically, antimalarial drugs are provided over the course of a 3 to 4 day regimen. Such multi-dose schedules are sub-optimal because it simply may not be feasible in the field where resources are often limited and dosing schedules may vary. Ideally drugs could be delivered in a single dose regimen that can be directly monitored to ensure compliance. Currently there are no drugs in clinical use for treatment of malaria with sufficient potency and safety to deliver cures following a single oral dose.

We evaluated ELQ-330 and ELQ-331 for their potential to cure mice of a patent malaria infection in a single dose, i.e., single dose cure (SDC), and compared our findings to the direct administration of the parent drug ELQ-300. As described above, mice (female, CF1, Charles River Labs) were infected intravenously with $10^5$ *P. yoelii* (Kenya strain, MR4 MRA-428/Murine LDH Elevating Virus-Free) parasitized erythrocytes from a donor animal. Drug administration commenced the day after the animals were inoculated (Day 1). The test compounds were dissolved in PEG-400 and administered by oral gavage once. On the 5th day blood films were prepared and the extent of parasitemia was determined by microscopic examination of Giemsa stained smears. Animals remaining parasite free 30 days after the last drug dose were considered cured of their infection.

In vivo studies were carried out as described above with ELQ-300 as an internal control. As previously published, while ELQ-300 is highly effective in low multi-dose regimens its poor aqueous solubility and high crystallinity prevent it from being useful as a single dose curative agent. In this experiment carried out at oral doses in the range of 1 to 20 mg/kg, ELQ-300 suppressed parasitemia completely however recrudescence occurred within two weeks of dosing. In comparison both ELQ-330 and ELQ-331 proved highly effective against murine malaria and superior to the parent drug ELQ-300. The lowest fully protective single-dose cure for ELQ-330 was achieved with an oral dose of 5 mg/kg and for ELQ-331 the lowest observable SDC was 2.5 mg/kg. Evaluation of ELQ-387 is currently being evaluated in this model. Taken together It is clear that the 4-position alkoxycarbonate ester derivatives of ELQ-300 are highly effective prodrugs that may be formulated for clinical use as antimalarial agents. Similar prodrug variants of other ELQs with clinical or veterinary potential should be more effective than the corresponding parent molecule, e.g., ELQ-271, ELQ-300, ELQ-316, and ELQ-400 etc., for treatment of malaria and other parasitic diseases including malaria (*falciparum, vivax, ovale, knowlesi,* and *malariae*), toxoplasmosis, babesiosis, coccidiosis, *theileria*, and other diseases caused by *Apicomplexan* parasites.

Example 6—6-chloro-7-methoxy-2-methyl-3-(4-(4-(trifluoromethoxy)phenoxy)phenyl)quinolin-4-yl ethyl Carbonate (ELQ-337)

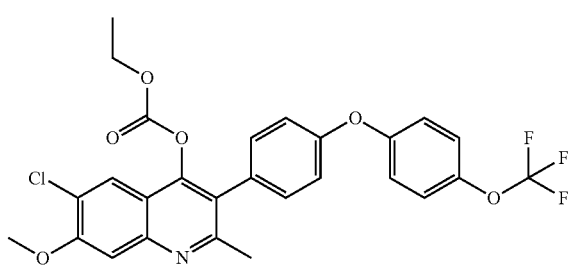 [SMILES: CCOC(=O)Oc1c(-c2ccc(Oc3ccc(OC(F)(F)F)cc3)cc2)c(C)nc2cc(OC)c(Cl)cc12]

To a flame dried 50 mL round bottom flask was added 0.5 g ELQ-300 (1.05 mmol, 1 eq), 84 mg sodium hydride (60% disp., 2.1 mmol, 2 eq) and anhydrous THF 5 mL. The resulting suspension was heated and stirred at 60° C. under argon atmosphere for 30 mins or until a clear solution was obtained. The reaction was removed from heat and 200 µL Ethyl chloroformate (2.1 mmol, 2 eq) was added dropwise via a syringe resulting in an immediate precipitation of white solids. The suspension was stirred for 5 mins and then quenched by dropwise addition of water. The reaction mixture was diluted with water (5 mL) and extracted with ethyl acetate (3×5 mL). The organic layer was washed with brine (5 mL) and dried over $MgSO_4$. The residue after evaporation was recrystallized (DCM, hexanes) to give 0.558 g ELQ-337 (6-chloro-7-methoxy-2-methyl-3-(4-(4-(trifluoromethoxy)phenoxy)phenyl)quinolin-4-yl ethyl carbonate) (97%) as white microcrystals. $^1$H NMR (400 MHz, $CDCl_3$) δ 7.89 (s, 1H), 7.50 (s, 1H), 7.32-7.27 (m, 2H), 7.23 (d, J=8.4 Hz, 2H), 7.15-7.01 (m, 4H), 4.16 (q, J=7.1 Hz, 2H), 4.06 (s, 3H), 2.54 (s, 3H), 1.22 (t, J=7.1 Hz, 3H).

Example 7—6-chloro-7-methoxy-2-methyl-3-(4-(4-(trifluoromethoxy)phenoxy)phenyl)quinolin-4-yl(2-methoxyethyl)carbonate (ELQ-354)

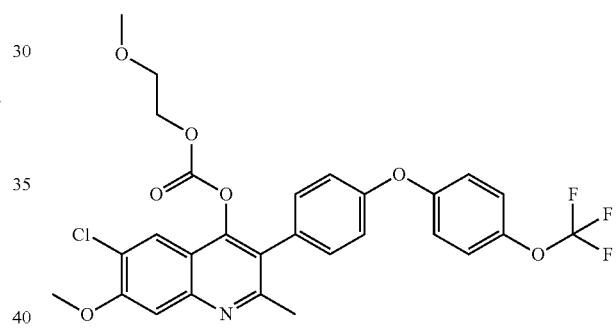

ELQ-354 was prepared according to the method of Example 6 except that 2 eq. 2-methoxyethyl chloroformate was used in place of ethyl chloroformate. $^1$H NMR (400 MHz, $CDCl_3$) δ 7.91 (bs, 1H), 7.52 (s, 1H), 7.29 (d, J=8.7 Hz, 2H), 7.24 (d, J=9.0 Hz, 2H), 7.14-7.04 (m, 4H), 4.31-4.20 (m, 2H), 4.07 (s, 4H), 3.57-3.49 (m, 2H), 3.37 (s, 3H), 1.25 (s, 3H).

Example 8—6-chloro-7-methoxy-2-methyl-3-(4-(4-(trifluoromethoxy)phenoxy)phenyl)quinolin-4-yl (2-(2-methoxyethoxy)ethyl)carbonate (ELQ-362)

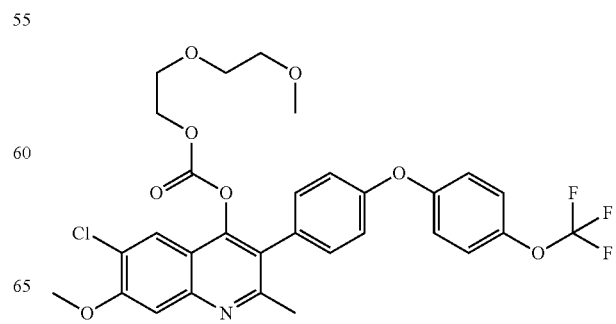

ELQ-362 was prepared according to the method of Example 6 except that 2 eq. 2-(2-methoxyethoxy)ethyl chloroformate was used in place of ethyl chloroformate. $^1$H NMR (400 MHz, CDCl$_3$) δ 7.90 (s, 1H), 7.52 (s, 1H), 7.33-7.27 (m, 2H), 7.23 (s, 2H), 7.15-7.05 (m, 4H), 4.30-4.19 (m, 2H), 4.06 (d, J=9.9 Hz, 4H), 3.68-3.58 (m, 4H), 3.57-3.50 (m, J=6.0, 3.0 Hz, 2H), 3.37 (s, 3H), 1.25 (s, 3H).

Example 9—6-chloro-7-methoxy-2-methyl-3-(4-(4-(trifluoromethoxy)phenoxy)phenyl)quinolin-4-yl (2-(2-(2-methoxyethoxy)ethoxy)ethyl)carbonate (ELQ-363)

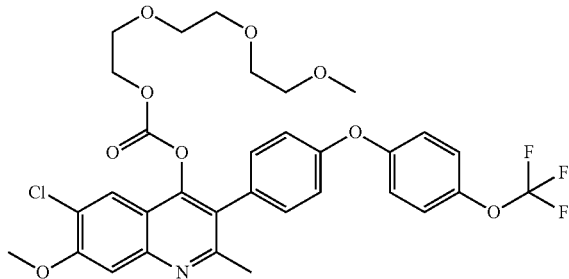 [SMILES: COCCOCCOCCOC(=O)Oc1c(-c2ccc(Oc3ccc(OC(F)(F)F)cc3)cc2)c(C)nc2cc(OC)c(Cl)cc12]

ELQ-363 Was prepared according to the method of Example 6 above except that 2 eq. 2-(2-(2-methoxyethoxy)ethoxy)ethyl chloroformate was used in place of ethyl chloroformate. $^1$H NMR (400 MHz, CDCl$_3$) δ 7.89 (s, 1H), 7.49 (bs, 1H), 7.28 (d, J=8.7 Hz, 2H), 7.24 (d, J=8.5 Hz, 2H), 7.13-7.06 (m, 4H), 4.27-4.22 (m, 2H), 4.06 (s, 3H), 3.68-3.60 (m, 8H), 3.54 (dd, J=5.7, 3.6 Hz, 2H), 3.37 (s, 3H), 1.25 (s, 3H).

Example 10—allyl (6-chloro-7-methoxy-2-methyl-3-(4-(4-(trifluoromethoxy)phenoxy)phenyl)quinolin-4-yl)carbonate (ELQ-359)

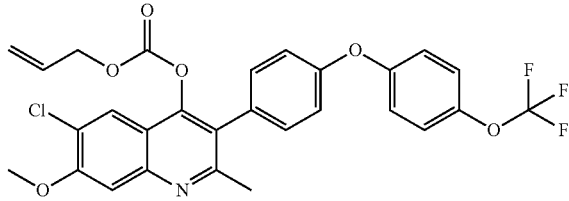 [SMILES: C=CCOC(=O)Oc1c(-c2ccc(Oc3ccc(OC(F)(F)F)cc3)cc2)c(C)nc2cc(OC)c(Cl)cc12]

ELQ-359 was prepared according to the method of Example 6 above except that 2 eq. allyl chloroformate in was used place of ethyl chloroformate. $^1$H NMR (400 MHz, CDCl$_3$) δ 7.89 (s, 1H), 7.52 (s, 1H), 7.28 (d, J=8.7 Hz, 2H), 7.23 (d, J=8.4 Hz, 2H), 7.14-7.02 (m, 4H), 5.79 (ddd, J=22.7, 11.0, 5.7 Hz, 1H), 5.31-5.26 (m, 1H), 5.23 (dd, J=10.6, 1.2 Hz, 1H), 4.58 (dt, J=5.7, 1.2 Hz, 2H), 4.06 (s, 3H), 2.54 (s, 3H).

Example 11—6-chloro-7-methoxy-2-methyl-3-(4-(4-(trifluoromethoxy)phenoxy)phenyl)quinolin-4-yl isobutyrate (ELQ-375)

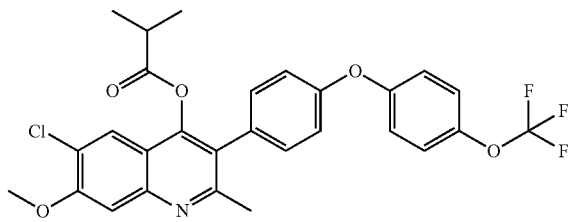 [SMILES: COc1cc2nc(C)c(-c3ccc(Oc4ccc(OC(F)(F)F)cc4)cc3)c(OC(=O)C(C)C)c2cc1Cl]

ELQ-375 was prepared according to the method of Example 6 above except that 2 eq. isobutyryl chloride was used in place of ethyl chloroformate. $^1$H NMR (400 MHz, CDCl$_3$) δ 8.50 (s, 1H), 7.86 (s, 1H), 7.25-7.02 (m, 8H), 4.19 (s, 3H), 2.88 (s, 3H), 2.71 (dq, J=13.8, 7.0 Hz, 1H), 1.08 (d, J=7.0 Hz, 6H).

Example 12—6-chloro-7-methoxy-2-methyl-3-(4-(4-(trifluoromethoxy)phenoxy)phenyl)quinolin-4-yl pivalate (ELQ-357)

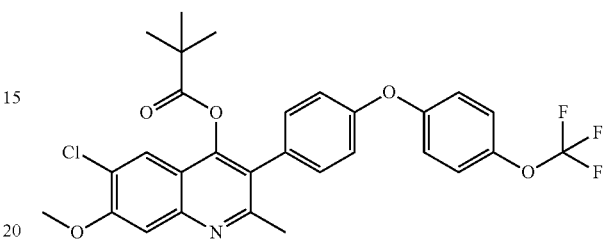

ELQ-357 was prepared according to the method of Example 6 above except that 2 eq. trimethylacetyl chloride was used in place of ethyl chloroformate. $^1$H NMR (400 MHz, CDCl$_3$) δ 8.35 (s, 1H), 7.78 (s, 1H), 7.25-7.01 (m, 8H), 4.17 (s, 3H), 2.80 (s, 3H), 1.15 (s, 9H).

Example 13—6-chloro-7-methoxy-2-methyl-3-(4-(4-(trifluoromethoxy)phenoxy)phenyl)quinolin-4-yl benzoate (ELQ-379)

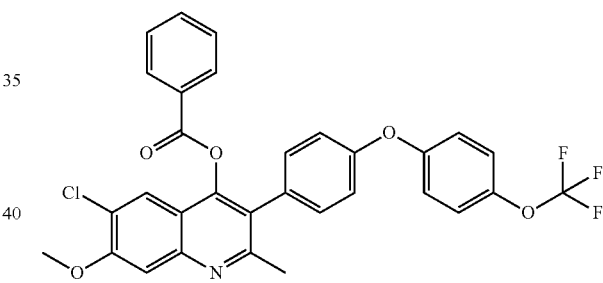

ELQ-379 was prepared according to the method of Example 6 above except 2 eq. Benzoyl chloride was used in place of ethyl chloroformate. $^1$H NMR (400 MHz, CDCl$_3$) δ 8.00 (dd, J=8.3, 1.2 Hz, 2H), 7.81 (s, 1H), 7.66 (dd, J=10.6, 4.4 Hz, 1H), 7.53 (s, 1H), 7.49 (t, J=7.8 Hz, 2H), 7.30 (d, J=8.7 Hz, 2H), 7.03 (dd, J=31.9, 8.5 Hz, 4H), 6.83-6.70 (m, 2H), 4.07 (s, 3H), 2.58 (s, 3H).

Example 14—tert-butyl (6-chloro-7-methoxy-2-methyl-3-(4-(4-(trifluoromethoxy)phenoxy)phenyl)quinolin-4-yl)carbonate (ELQ-358)

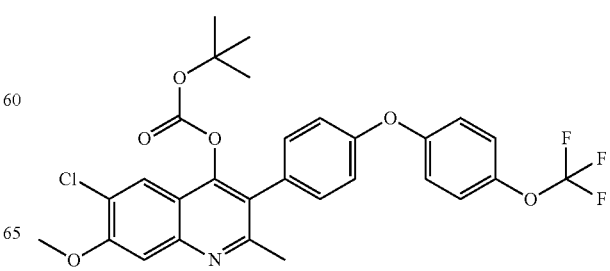

ELQ-358 was prepared according to the method of Example 6 above except that 2 eq. di-tert-butyl dicarbonate was used in place of ethyl chloroformate. ¹H NMR (400 MHz, CDCl₃) δ 7.90 (s, 1H), 7.49 (s, 1H), 7.32-7.28 (m, 2H), 7.25-7.20 (m, 2H), 7.13-7.03 (m, 4H), 4.06 (s, 3H), 2.54 (s, 3H), 1.37 (s, 9H)

Example 15—6-chloro-7-methoxy-2-methyl-3-(4-(4-(trifluoromethoxy)phenoxy)phenyl)quinolin-4-yl ((2,2-dimethyl-1,3-dioxolan-4-yl)methyl)carbonate (ELQ-374)

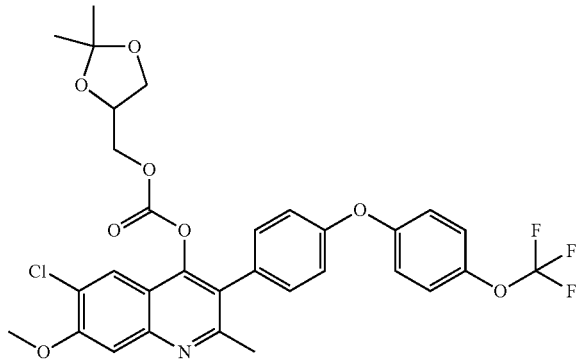 [SMILES: COc1cc2nc(C)c(-c3ccc(Oc4ccc(OC(F)(F)F)cc4)cc3)c(OC(=O)OCC3COC(C)(C)O3)c2cc1Cl]

ELQ-374 was prepared according to the method of Example 6 above except that 2 eq. (2,2-dimethyl-1,3-dioxolan-4-yl)methyl chloroformate was used in place of ethyl chloroformate. ¹H NMR (400 MHz, CDCl₃) δ 7.90 (s, 1H), 7.52 (s, 1H), 7.28 (d, J=8.6 Hz, 2H), 7.24 (d, J=9.3 Hz, 2H), 7.10 (dd, J=8.8, 1.7 Hz, 4H), 4.23-4.08 (m, 3H), 4.06 (s, 3H), 4.01 (dd, J=8.6, 6.3 Hz, 1H), 3.64 (dd, J=8.6, 5.3 Hz, 1H), 2.54 (s, 3H), 1.40 (s, 3H), 1.37 (s, 3H).

Example 16—6-chloro-7-methoxy-2-methyl-3-(4-(4-(trifluoromethoxy)phenoxy)phenyl)quinolin-4-yl (2,3-dihydroxypropyl)carbonate (ELQ-376)

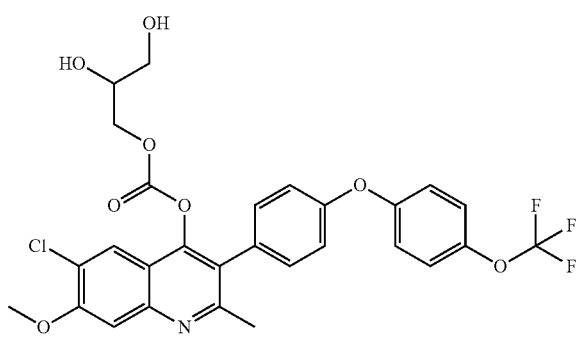 [SMILES: COc1cc2nc(C)c(-c3ccc(Oc4ccc(OC(F)(F)F)cc4)cc3)c(OC(=O)OCC(O)CO)c2cc1Cl]

ELQ-376 was prepared according to the method of Example 6 above, except that 2 eq. (2-oxo-1,3-dioxolan-4-yl)methyl chloroformate was used in place of ethyl chloroformate. ¹H NMR (400 MHz, CDCl₃) δ 7.85 (s, 1H), 7.50 (s, 1H), 7.27 (t, J=8.0 Hz, 4H), 7.17-7.05 (m, 4H), 4.79 (ddt, J=8.4, 6.2, 4.1 Hz, 1H), 4.48 (t, J=8.7 Hz, 1H), 4.31 (qd, J=12.4, 4.0 Hz, 2H), 4.07 (t, J=7.5 Hz, 1H), 4.06 (s, 3H), 2.54 (s, 3H).

Example 17—6-chloro-7-methoxy-2 methyl-3-(4-(4-(trifluoromethoxy)phenoxy)phenyl)quinolin-4-yl ((2-oxo-1,3-dioxolan-4-yl)methyl)carbonate (ELQ-373)

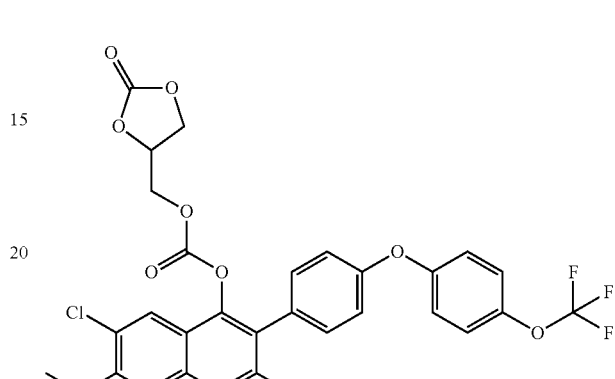

ELQ-373 was prepared from 6-chloro-7-methoxy-2-methyl-3-(4-(4(trifluoromethoxy)phenoxy)phenyl)quinolin-4-yl((2,2-dimethyl-1,3-dioxolan-4-yl)methyl)carbonate upon stirring in 2M HCl for 12h. ¹H NMR (400 MHz, CDCl₃) δ 7.79 (s, 1H), 7.44 (s, 1H), 7.27-7.11 (m, 4H), 7.11-7.00 (m, 4H), 4.72 (ddt, J=8.3, 6.2, 4.1 Hz, 1H), 4.41 (t, J=8.7 Hz, 1H), 4.24 (qd, J=12.3, 3.9 Hz, 2H), 4.00 (s, 3H), 4.04-3.93 (m, 1H), 2.48 (s, 3H).

Example 18—6-chloro-7-methoxy-2-methyl-3-(4-(4-(trifluoromethoxy)phenoxy)phenyl)quinolin-4-yl (1,1-dioxidotetrahydrothiophen-3-yl)carbonate (ELQ-355)

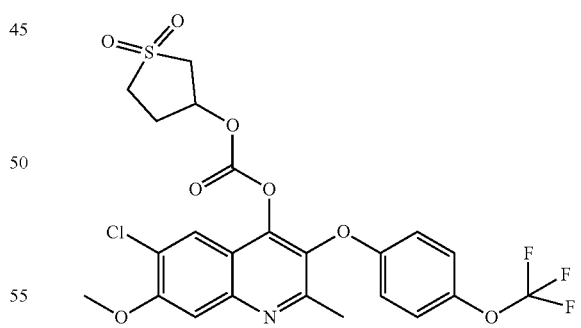

ELQ-355 was prepared according to the method of Example 6 above, except that 2 eq. 1,1-dioxidotetrahydrothiophen-3-yl chloroformate was used in place of ethyl chloroformate. ¹H NMR (400 MHz, CDCl₃) δ 7.88 (s, 1H), 7.52 (s, 1H), 7.39-7.27 (m, J=2.6 Hz, 4H), 7.12 (dd, J=13.0, 8.9 Hz, 4H), 5.36-5.22 (m, 1H), 4.07 (s, 3H), 3.30 (dd, J=14.7, 6.5 Hz, 1H), 3.12 (dd, J=9.6, 5.8 Hz, 2H), 2.91 (d, J=14.6 Hz, 1H), 2.56 (s, 3H), 2.50-2.38 (m, 1H), 2.35-2.22 (m, 1H).

Example 19—6-chloro-7-methoxy-2-methyl-3-(4-(4-(trifluoromethoxy)phenoxy)phenyl)quinolin-4-yl methyl carbonate (ELQ-336)

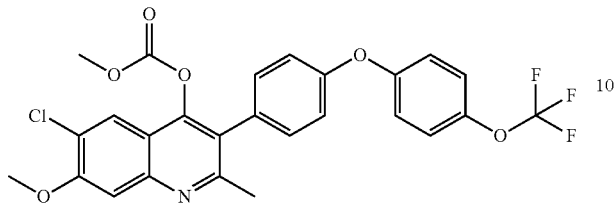

ELQ-336 was prepared according to the method of Example 6 above, except that 2 eq. methyl chloroformate was used in place of ethyl chloroformate. $^1$H NMR (400 MHz, CDCl$_3$) δ 7.88 (s, 1H), 7.51 (s, 1H), 7.30-7.27 (m, 2H), 7.24 (d, J=8.4 Hz, 2H), 7.13-7.05 (m, 4H), 4.06 (s, 3H), 3.75 (s, 3H), 2.54 (s, 3H).

Example 20—6-fluoro-7-methoxy-2-methyl-3-(4-(4-(trifluoromethoxy)phenoxy)phenyl)quinolin-4-yl ethyl carbonate (ELQ-334)

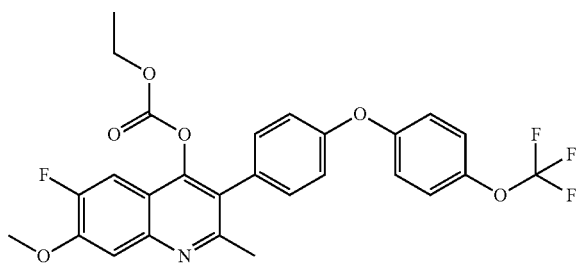

ELQ-334 was prepared according to the method of Example 6 above from 6-fluoro-7-methoxy-2-methyl-3-(4-(4-(trifluoromethoxy)phenoxy)phenyl)quinolin-4-ol and ethyl chloroformate. $^1$H-NMR (400 MHz; CDCl$_3$): δ 7.52 (d, J=8.0 Hz, 1H), 7.48 (d, J=11.2 Hz, 1H), 7.30-7.27 (m, 2H), 7.24-7.22 (m, 2H), 7.12-7.06 (m, 4H), 4.15 (q, J=7.1 Hz, 2H), 4.04 (s, 3H), 2.53 (s, 3H), 1.22 (t, J=7.1 Hz, 3H). $^{19}$F-NMR (376 MHz; CDCl$_3$): δ −58.26 (s, 1F), −131.68 (t, J=9.9 Hz,).

Example 21—6-fluoro-7-methoxy-2-methyl-3-(4-(4-(trifluoromethoxy)phenoxy)phenyl)quinolin-4-yl pivalate (ELQ-377)

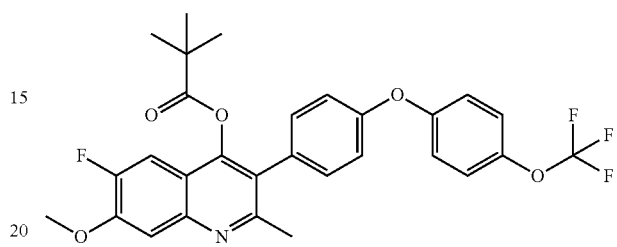

ELQ-377 was prepared according to the method of Example 6 above from 6-fluoro-7-methoxy-2-methyl-3-(4-(4-(trifluoromethoxy)phenoxy)phenyl)quinolin-4-ol and trimethylacetyl chloride $^1$H NMR (400 MHz, CDCl$_3$) δ 7.51 (d, J=8.0 Hz, 1H), 7.28 (s, 1H), 7.25-7.19 (m, 4H), 7.12-7.00 (m, 4H), 4.04 (s, 3H), 2.49 (s, 3H), 1.14 (s, 9H).

Example 22—Efficacy of ELQ-337 In Vitro and In Vivo

In vitro experiments show that the intrinsic antiplasmodial activity of ethylcarbonate ester ELQ-337 is indistinguishable from ELQ-300, with IC$_{50}$ values against all test strains in the low to sub-nanomolar range. In vivo experiments using the 4-day suppression test protocol (dosing on 4 sequential days with smears on Day 5) vs. *P. yoelii* infected mice show that the action profile is unchanged at lower doses needed for ED$_{50}$ (0.02 mg/kg/d), ED$_{90}$ (0.05 mg/kg/d), ED$_{99}$ (0.075 mg/kg/d), and non-recrudescence dose remains impressive (0.3 to 1 mg/kg/d). Importantly and unlike ELQ-300 (at any dose), ELQ-337 provided 4/4 single dose cures (SDC) at doses as low as 3 mg/kg (1 mg/kg failed in 4/4 animals on Day 12).

TABLE 1

Efficacy of exemplary compounds.

| Code | Chemical Structure | $c_{log}P$ | *P. falciparum* strain D6, IC$_{50}$, nM | Lowest fully effective single dose cure P. yoelii (mg/kg) |
|---|---|---|---|---|
| ELQ-300 | 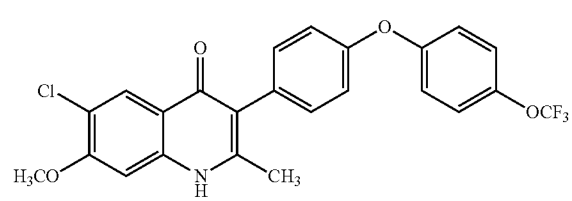 [SMILES: COc1cc2[nH]c(C)c(-c3ccc(Oc4ccc(OC(F)(F)F)cc4)cc3)c(=O)c2cc1Cl] | 5.66 | 3.1 | >20* |

TABLE 1-continued

Efficacy of exemplary compounds.

| Code | Chemical Structure | $c_{log}P$ | P. falciparum strain D6, IC$_{50}$, nM | Lowest fully effective single dose cure P. yoelii (mg/kg) |
| --- | --- | --- | --- | --- |
| ELQ-336 | 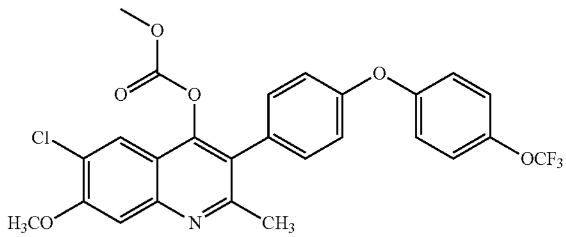 [SMILES: COC(=O)Oc1c(-c2ccc(Oc3ccc(OC(F)(F)F)cc3)cc2)c(C)nc2cc(OC)c(Cl)cc12] | 8.16 | 2.5 | 4 |
| ELQ-337 | 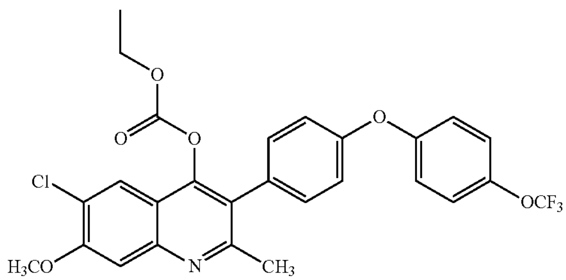 [SMILES: CCOC(=O)Oc1c(-c2ccc(Oc3ccc(OC(F)(F)F)cc3)cc2)c(C)nc2cc(OC)c(Cl)cc12] | 8.5 | 2.5 | 3 |
| ELQ-354 | 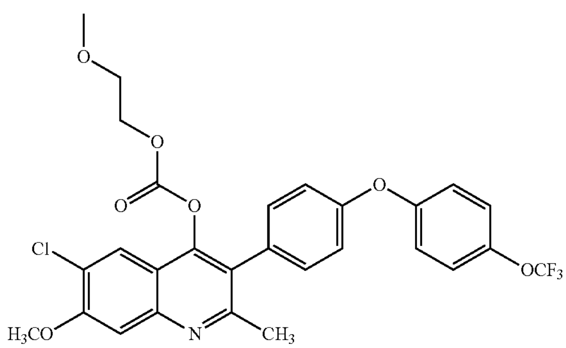 [SMILES: COCCOC(=O)Oc1c(-c2ccc(Oc3ccc(OC(F)(F)F)cc3)cc2)c(C)nc2cc(OC)c(Cl)cc12] | 7.2 | 3.0 | 3 |
| ELQ-355 | 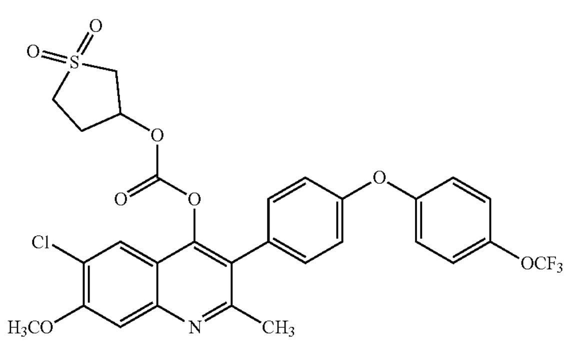 [SMILES: COc1cc2nc(C)c(-c3ccc(Oc4ccc(OC(F)(F)F)cc4)cc3)c(OC(=O)OC3CCS(=O)(=O)C3)c2cc1Cl] | 5.8 | 3.9 | 4 |
| ELQ-357 | 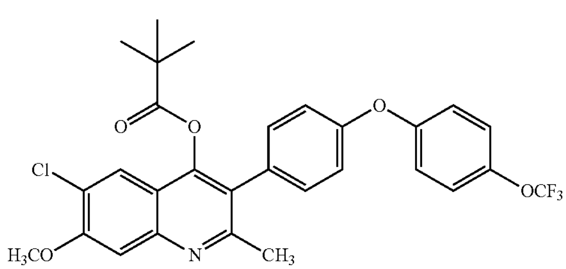 [SMILES: COc1cc2nc(C)c(-c3ccc(Oc4ccc(OC(F)(F)F)cc4)cc3)c(OC(=O)C(C)(C)C)c2cc1Cl] | 8.5 | 3.5 | 4 |

TABLE 1-continued

Efficacy of exemplary compounds.

| Code | Chemical Structure | $c_{log}P$ | P. falciparum strain D6, $IC_{50}$, nM | Lowest fully effective single dose cure P. yoelii (mg/kg) |
|---|---|---|---|---|
| ELQ-358 | 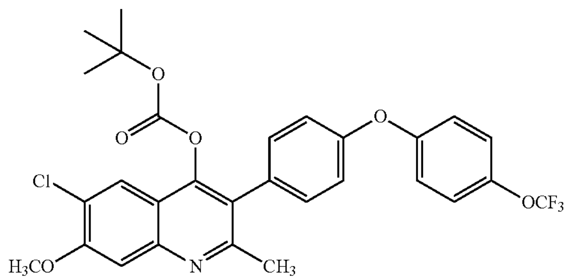 [SMILES: COc1cc2nc(C)c(-c3ccc(Oc4ccc(OC(F)(F)F)cc4)cc3)c(OC(=O)OC(C)(C)C)c2cc1Cl] | 8.3 | 6.0 | >4 |
| ELQ-359 | 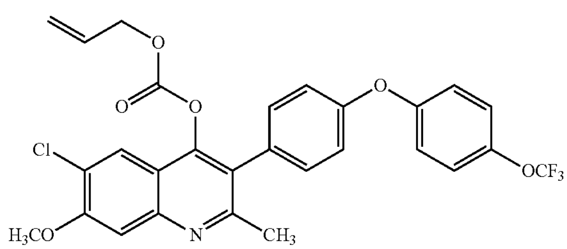 [SMILES: C=CCOC(=O)Oc1c(-c2ccc(Oc3ccc(OC(F)(F)F)cc3)cc2)c(C)nc2cc(OC)c(Cl)cc12] | 7.9 | 2.5 | 4 |
| ELQ-373 | 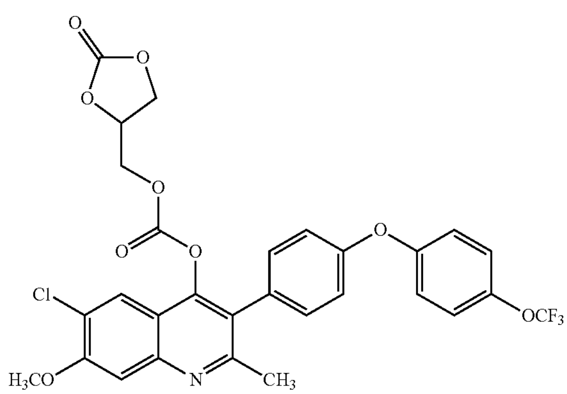 [SMILES: COc1cc2nc(C)c(-c3ccc(Oc4ccc(OC(F)(F)F)cc4)cc3)c(OC(=O)OCC3COC(=O)O3)c2cc1Cl] | 6.2 | 3.1 | 4 |
| ELQ-374 | 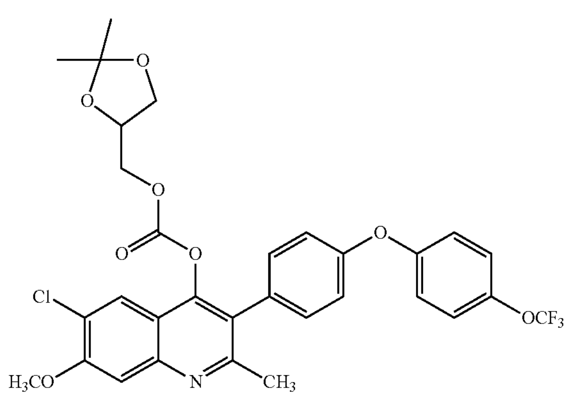 [SMILES: COc1cc2nc(C)c(-c3ccc(Oc4ccc(OC(F)(F)F)cc4)cc3)c(OC(=O)OCC3COC(C)(C)O3)c2cc1Cl] | 8.0 | 2.7 | 4 |

TABLE 1-continued
Efficacy of exemplary compounds.
| Code | Chemical Structure | $c_{log}P$ | *P. falciparum* strain D6, $IC_{50}$, nM | Lowest fully effective single dose cure P. yoelii (mg/kg) |
|---|---|---|---|---|
| ELQ-375 | 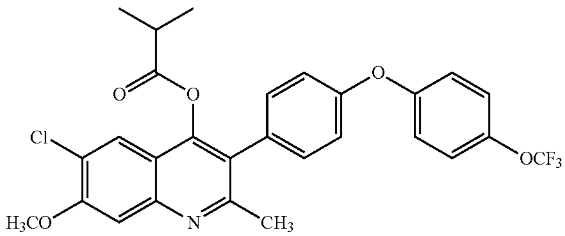 [SMILES: COc1cc2nc(C)c(-c3ccc(Oc4ccc(OC(F)(F)F)cc4)cc3)c(OC(=O)C(C)C)c2cc1Cl] | 8.1 | 8.2 | 4 |
| ELQ-379 | 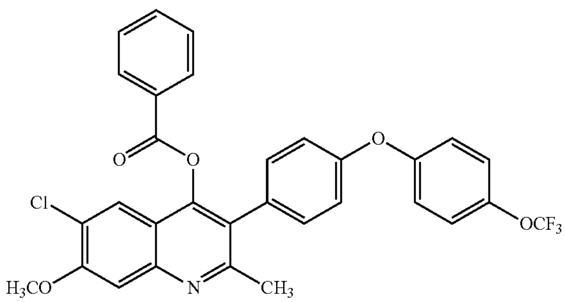 [SMILES: COc1cc2nc(C)c(-c3ccc(Oc4ccc(OC(F)(F)F)cc4)cc3)c(OC(=O)c3ccccc3)c2cc1Cl] | 9.4 | 2.5 | ND |
The invention claimed is:
1. A compound selected from the group of:
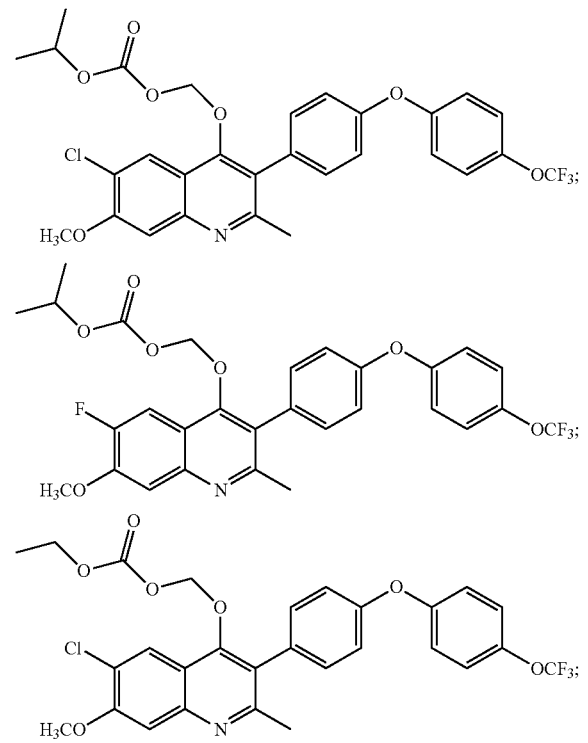
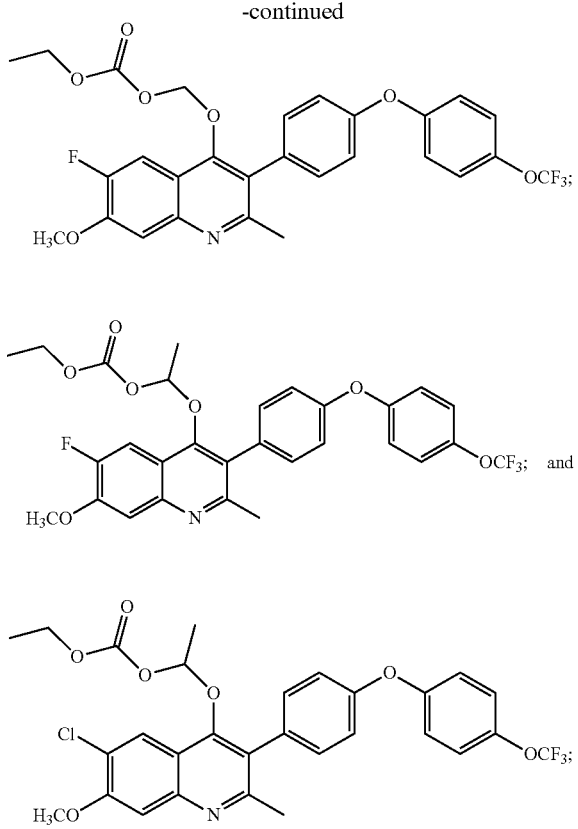
or a pharmaceutically acceptable salt thereof.

2. The compound of claim 1 selected from the group of:
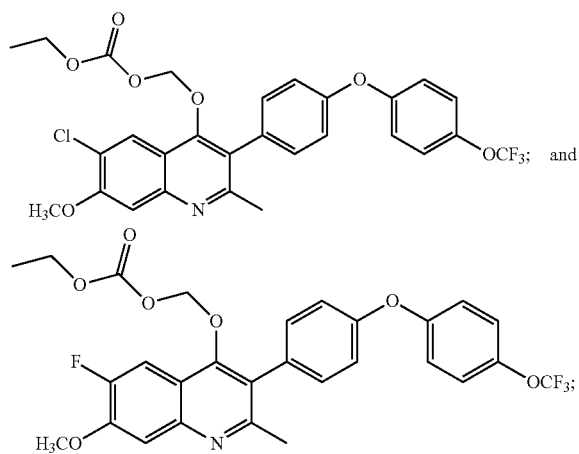
or a pharmaceutically acceptable salt thereof.
3. The compound of claim 1 which is:
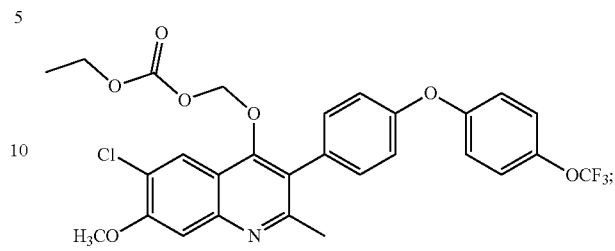
or a pharmaceutically acceptable salt thereof.
* * * * *

UNITED STATES PATENT AND TRADEMARK OFFICE
CERTIFICATE OF CORRECTION

| | |
|---|---|
| PATENT NO. | : 10,584,098 B2 |
| APPLICATION NO. | : 16/110956 |
| DATED | : March 10, 2020 |
| INVENTOR(S) | : Michael Riscoe et al. |

It is certified that error appears in the above-identified patent and that said Letters Patent is hereby corrected as shown below:

In the Specification

At Column 1, Lines 16-24, within the ACKNOWLEDGEMENT OF GOVERNMENT SUPPORT, please replace:
"Work resulting in this invention was funded by the United States government under the terms of a VA Merit Review Grant awarded to Dr. Michael Riscoe by the United States Veterans Administration and Grant Numbers R56AI100569, R01AI100569, and PR130649 awarded by the National Institutes of Health. The United States government has certain rights in this invention."

With:
-- This invention was made with government support under R56 AI100569 and R01 AI100569 awarded by the National Institutes of Health and W81XWH-14-1-0447 awarded by the Department of Defense. The government has certain rights in the invention. --

Signed and Sealed this
Twenty-ninth Day of August, 2023

Katherine Kelly Vidal
*Director of the United States Patent and Trademark Office*